US012569139B2

(12) United States Patent

Sekowski

(10) Patent No.: US 12,569,139 B2

(45) Date of Patent: *Mar. 10, 2026

(54) MICROSURGICAL SYSTEMS FOR PERFORMING SURGICAL PROCEDURES

(71) Applicant: Marek Sekowski, Gig Harbor, WA (US)

(72) Inventor: Marek Sekowski, Gig Harbor, WA (US)

( * ) Notice: Subject to any disclaimer, the term of this patent is extended or adjusted under 35 U.S.C. 154(b) by 351 days.

This patent is subject to a terminal disclaimer.

(21) Appl. No.: 18/143,494

(22) Filed: May 4, 2023

(65) Prior Publication Data

US 2023/0270335 A1     Aug. 31, 2023

Related U.S. Application Data

(62) Division of application No. 16/252,628, filed on Jan. 19, 2019, now Pat. No. 11,672,424.

(51) Int. Cl.
A61B 5/00          (2006.01)
A61B 1/00          (2006.01)
(Continued)

(52) U.S. Cl.
CPC ........ A61B 5/0075 (2013.01); A61B 1/00045 (2013.01); A61B 1/00087 (2013.01);
(Continued)

(58) Field of Classification Search
CPC ... A61B 5/0075; A61B 90/37; A61B 1/00045; A61B 1/00087; A61B 1/00114; A61B 1/00119; A61B 1/00135; A61B 1/05; A61B 1/063; A61B 1/0638; A61B 1/0684; A61B 1/07; A61B 1/00167; A61B 2090/373
(Continued)

(56) References Cited

U.S. PATENT DOCUMENTS

| 1,627,941 A | 5/1927 | Wappler |
| 2,691,370 A | 10/1954 | Joseph |

(Continued)

FOREIGN PATENT DOCUMENTS

| WO | 2013043734 A1 | 3/2013 |
| WO | 2014145120 A1 | 9/2014 |

(Continued)

*Primary Examiner* — Beverly M Flanagan

(74) *Attorney, Agent, or Firm* — James A Cardle

(57)          ABSTRACT

In various aspects, a microsurgical apparatus disclosed herein includes a shaft having a shaft distal end, a shaft proximal end with a handle mounted to shaft proximal end. The microsurgical apparatus includes a tool package having an actuator at a tool package proximal end of the tool package and a tool at a tool package distal end of the tool package. The actuator cooperates mechanically with the tool. A sleeve lumen disposed within the tool package slidably receives the shaft for releasable lockable engagement of the tool package proximal end with the handle and with the shaft distal end being generally coextensive with the tool package distal end. Light source(s) and image sensor(s) located proximate the shaft distal end allow viewing of regions distal to the shaft including the tool when the tool package is mounted to the shaft. Exemplary methods of use of the microsurgical apparatus are also disclosed herein.

20 Claims, 20 Drawing Sheets

(51) Int. Cl.

| | |
|---|---|
| *A61B 1/05* | (2006.01) |
| *A61B 1/06* | (2006.01) |
| *A61B 1/07* | (2006.01) |
| *A61B 90/00* | (2016.01) |

(52) U.S. Cl.
CPC ...... *A61B 1/00114* (2013.01); *A61B 1/00119* (2013.01); *A61B 1/00135* (2013.01); *A61B 1/05* (2013.01); *A61B 1/063* (2013.01); *A61B 1/0638* (2013.01); *A61B 1/0684* (2013.01); *A61B 1/07* (2013.01); *A61B 90/37* (2016.02); *A61B 1/00167* (2013.01); *A61B 2090/373* (2016.02)

(58) Field of Classification Search
USPC .......................................................... 606/41
See application file for complete search history.

(56) References Cited

U.S. PATENT DOCUMENTS

| | | | |
|---|---|---|---|
| 4,027,510 | A | 6/1977 | Hiltebrandt |
| 4,300,564 | A | 11/1981 | Furihata |
| 4,471,766 | A | 9/1984 | Terayama |
| 4,759,348 | A | 7/1988 | Cawood |
| 5,471,237 | A | 11/1995 | Shipp |
| 5,538,497 | A | 7/1996 | Hori |
| 5,549,542 | A | 8/1996 | Kovalcheck |
| 5,591,192 | A | 1/1997 | Privitera et al. |
| 5,643,175 | A | 7/1997 | Adair |
| 5,718,664 | A | 2/1998 | Peck et al. |
| 5,746,770 | A | 5/1998 | Zeitels et al. |
| 5,752,972 | A | 5/1998 | Hoogeboom |
| 5,928,137 | A | 7/1999 | Green |
| 6,052,190 | A | 4/2000 | Sekowski et al. |
| 6,086,528 | A | 7/2000 | Adair |
| 6,100,920 | A | 8/2000 | Miller et al. |
| 6,419,626 | B1 | 7/2002 | Yoon |
| 6,749,559 | B1 | 6/2004 | Kraas et al. |
| 7,029,435 | B2 | 4/2006 | Nakao |
| 7,780,690 | B2 | 8/2010 | Rehnke |
| 7,951,069 | B2 | 5/2011 | Bertolero |
| 8,152,715 | B2 | 4/2012 | Root et al. |
| 8,409,200 | B2 | 4/2013 | Holcomb et al. |
| 8,585,584 | B2 | 11/2013 | Ratnakar |
| 8,602,980 | B2 | 12/2013 | Bassan et al. |
| 8,696,552 | B2 | 4/2014 | Whitman |
| 8,721,529 | B2 | 5/2014 | Hess et al. |
| 8,932,208 | B2 | 1/2015 | Kendale et al. |
| 8,942,530 | B2 | 1/2015 | Demers et al. |
| 9,101,266 | B2 | 8/2015 | Levi et al. |
| 9,320,419 | B2 | 4/2016 | Kirma et al. |
| 9,433,342 | B2 | 9/2016 | Perretta et al. |
| 9,468,456 | B2 | 10/2016 | Raybin et al. |
| 9,549,662 | B2 | 1/2017 | Demers et al. |
| 9,706,903 | B2 | 7/2017 | Kirma et al. |
| 9,848,761 | B2 | 12/2017 | Demers et al. |
| 9,968,249 | B2 | 5/2018 | Huang et al. |
| 10,121,820 | B1 | 11/2018 | Chen et al. |
| 10,835,360 | B2 | 11/2020 | Sekowski |
| 11,672,424 | B2 * | 6/2023 | Sekowski ........... A61B 5/0075 600/106 |
| 2002/0156465 | A1 | 10/2002 | Overaker et al. |
| 2007/0213590 | A1 | 9/2007 | Squicciarini |
| 2008/0188890 | A1 | 8/2008 | Weitzner et al. |
| 2008/0306333 | A1 | 12/2008 | Chin |
| 2009/0131907 | A1 | 5/2009 | Chin et al. |
| 2010/0091094 | A1 | 4/2010 | Sekowski |
| 2011/0295061 | A1 | 12/2011 | Haramaty et al. |
| 2011/0313245 | A1 | 12/2011 | Scholly et al. |
| 2013/0071077 | A1 | 3/2013 | Demers et al. |
| 2013/0345510 | A1 | 12/2013 | Hadani |
| 2014/0005654 | A1 | 1/2014 | Batross et al. |
| 2014/0055562 | A1 | 2/2014 | Demers et al. |
| 2014/0055582 | A1 | 2/2014 | Demers et al. |
| 2014/0142592 | A1 | 5/2014 | Moon et al. |
| 2014/0336456 | A1 | 11/2014 | Demers et al. |
| 2014/0336465 | A1 | 11/2014 | Demers et al. |
| 2015/0009357 | A1 | 1/2015 | Seibel et al. |
| 2015/0119644 | A1 | 4/2015 | Demers et al. |
| 2015/0142041 | A1 | 5/2015 | Kendale et al. |
| 2016/0000309 | A1 | 1/2016 | Weber et al. |
| 2016/0081705 | A1 | 3/2016 | Furlong et al. |
| 2016/0310042 | A1 | 10/2016 | Kesten et al. |
| 2016/0331216 | A1 | 11/2016 | Kaneko |
| 2016/0367311 | A1 * | 12/2016 | Gerrans ................. A61B 10/02 |
| 2017/0224199 | A1 | 8/2017 | Demers et al. |
| 2017/0280986 | A1 | 10/2017 | Sekowski et al. |
| 2018/0110404 | A1 | 4/2018 | Devaiah et al. |
| 2018/0125344 | A1 | 5/2018 | Sekowski et al. |
| 2018/0228345 | A1 | 8/2018 | Sekowski et al. |
| 2018/0228346 | A1 | 8/2018 | Sekowski et al. |

FOREIGN PATENT DOCUMENTS

| | | |
|---|---|---|
| WO | 2016064449 A1 | 4/2016 |
| WO | 2016064763 A1 | 4/2016 |
| WO | 2016171780 A1 | 10/2016 |
| WO | 2017173179 A1 | 10/2017 |

* cited by examiner

MICROSURGICAL SYSTEMS FOR PERFORMING SURGICAL PROCEDURES

CROSS-REFERENCE TO RELATED APPLICATIONS

The present application is a continuation of U.S. patent application Ser. No. 16/252,628 filed 19 Jan. 2019, which is hereby incorporated by reference in its entirety herein.

BACKGROUND OF THE INVENTION

Field

The present disclosure relates to medical devices, and, more particularly, to microsurgical systems for performing surgical procedures.

Background

A common problem with current devices used in micro-surgery including endoscopic surgery is the viewing of the surgical area of interest. Viewing devices such as magnifying loops or microscopes may cost upwards of $1/2 million. Apart from expense, current viewing devices may restrict a physician's upper body movement during surgical procedures because the physician is required to maintain a fixed position in order to view through the viewing device, which may lead to chronic neck or back problems.

A viewing device such as a magnifying loop having more than 3× magnification may be required for certain surgical procedures. As the magnification increases, the field of view of the viewing device is correspondingly limited, thereby forcing the physician to constantly adjust the position and magnification of the viewing device during the surgical procedure.

A variety of different tools may be used during the course of a microsurgical procedure. These tools may be expensive and difficult to sterilize. Furthermore, the tools may be separate from the viewing device, so that the physician must coordinate the viewing device and the tools in order to keep the tools within the field of view of the viewing device during surgery.

Accordingly, there is a need for improved apparatus as well as related methods for microsurgery.

BRIEF SUMMARY OF THE INVENTION

These and other needs and disadvantages may be overcome by the microsurgical apparatus and related methods of use of the microsurgical apparatus disclosed herein. Additional improvements and advantages may be recognized by those of ordinary skill in the art upon study of the present disclosure.

In various aspects, the microsurgical apparatus includes a shaft having a shaft distal end, a shaft proximal end, and a constant cross-section. A handle is mounted to the shaft proximal end, in various aspects. In various aspects, the microsurgical apparatus includes a tool package with an actuator at a tool package proximal end of the tool package and a tool at a tool package distal end of the tool package. The actuator cooperates mechanically with the tool to alter the tool between a disengaged position and an engaged position as the actuator is altered between a first actuator position and a second actuator position, in various aspects. In various aspects, a sleeve disposed within the tool package forms a sleeve lumen that extends between the tool package proximal end and the tool package distal end. When the sleeve lumen insertably receives the shaft, the tool package proximal end is releaseably lockably engaged with the handle, and an image sensor disposed at the shaft distal end views at least portions of the tool illuminated by a light source disposed at the shaft distal end, in various aspects.

Exemplary methods of use of the microsurgical apparatus may include the steps of slidably receiving the tool package over the shaft and lockably releasably engaging the tool package with the handle. Exemplary methods of use may include the steps of diagnosing, treating, or diagnosing and treating a patient using a tool at a tool package distal end of the tool package. Image sensor(s) illuminated by light source(s) located at the shaft distal end may be used to guide the tool into position or to view the tool and surrounding environs during diagnosis or therapy. Exemplary methods of use of the microsurgical apparatus may include the step of disengaging the tool package from the handle following use and the step of removing the tool package from the shaft. The tool package may then be discarded following removal from the shaft. Exemplary methods of use of the microsurgical apparatus may include the step of slidably receiving a different tool package over the shaft in lockable releasable engagement with the handle following removal of the tool package.

This summary is presented to provide a basic understanding of some aspects of the apparatus and related methods disclosed herein as a prelude to the detailed description that follows below. Accordingly, this summary is not intended to identify key elements of the apparatus and methods disclosed herein or to delineate the scope thereof.

Figure 1:
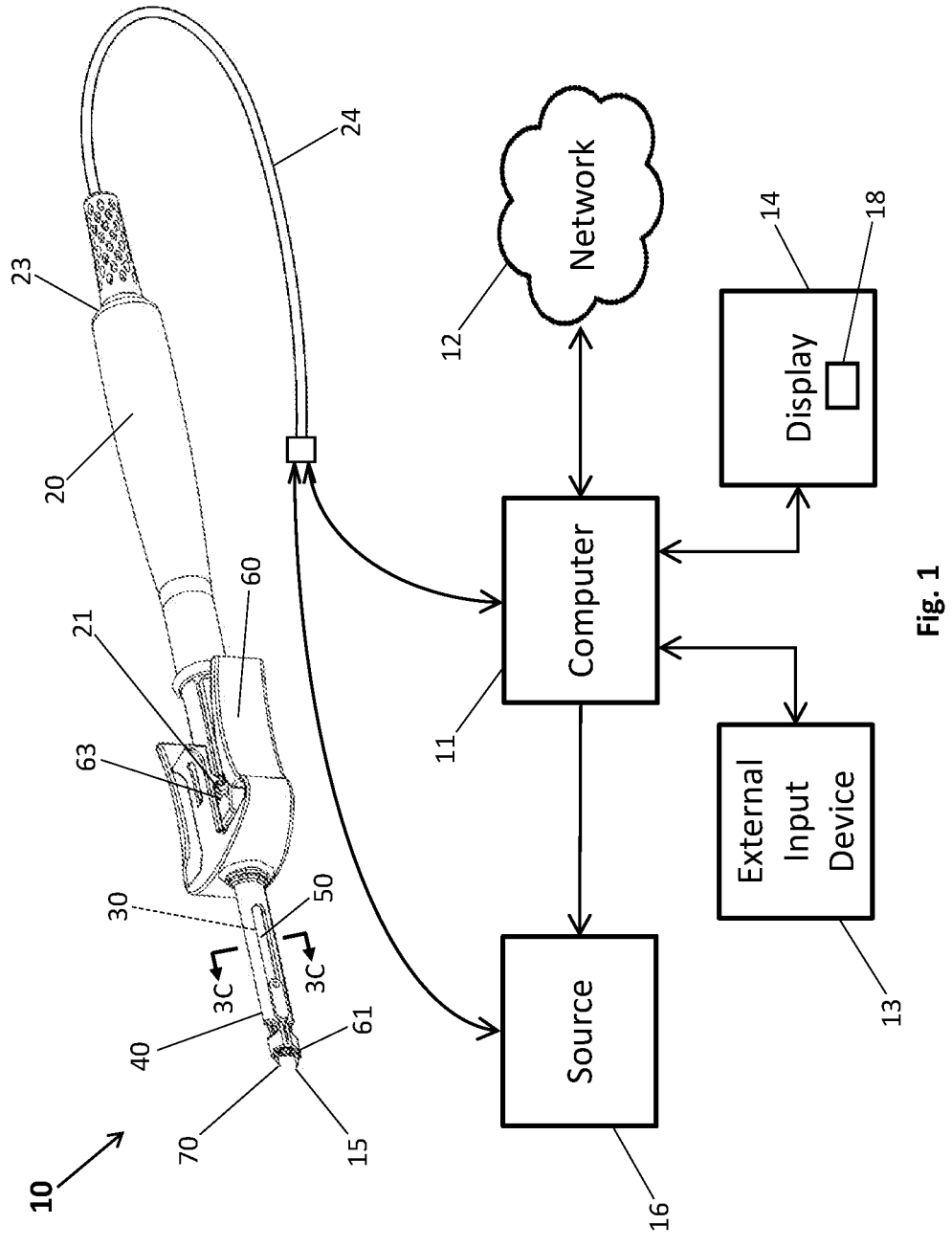
FIG. 1 illustrates by perspective view in combination with a schematic diagram an exemplary implementation of a microsurgical apparatus.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as +0.1%, +1%, +2.5%, +5%, or other such tolerances, as would be readily recognized by those of ordinary skill in the art upon study of this disclosure.

DETAILED DESCRIPTION OF THE INVENTION

A microsurgical apparatus is disclosed herein. In various aspects, the microsurgical apparatus includes a handle with a shaft mounted to the handle distal end, and a tool package. The tool package includes an actuator at a tool package proximal end of the tool package and a tool at a tool package distal end of the tool package, in various aspects. The tool package, in various aspects, is slidably received over the shaft and then releasably lockably engaged with the handle. The tool package may be released from engagement with the handle, removed from the shaft, and replaced with a different tool package that may have a different tool, in various aspects. Once removed, the tool package may be discarded.

The tool, in various aspects, may include grippers for the manipulation of tissue, scissors, scalpel, or saw for the cutting of tissue including bone and soft tissue, electrodes for bipolar electrosurgery oblation and cauterization, or lumen for argon cryo-ablation. Various lumen may be provided about the tool package for the communication of fluids with distal portions of the tool package, for example, in order to provide suction, irrigation, or cryogenic fluids. Electrical pathways may be provided about the tool package for electrical communication with, for example, the tool package distal end including the tool. Fiberoptic pathways may be provided about the tool package for communication of light with, for example, the tool package distal end including the tool. One or more light sources may be located proximate the shaft distal end to illuminate the tool and surrounding environs during surgical procedures, and one or more image sensors may be located proximate the shaft distal end to allow viewing of the tool and surrounding environs during surgical procedures, in various aspects. Various fluid pathways, electrical pathways, and fiberoptic pathways may pass within the shaft, in various aspects.

In various aspects, the actuator cooperates mechanically with the tool to alter the tool between a disengaged position and an engaged position as the actuator is altered between a first actuator position and a second actuator position.

In various aspects, the microsurgical apparatus disclosed herein may, for example, be used in neurological surgery such as brain surgery and spine surgery, orthopedic surgery such as trigger finger, carpal tunnel, and knee arthroscopy, various urologic procedures, various procedures directed at the female reproductive organs, and various pediatric procedures including procedures within the womb.

As used herein, the terms distal and proximal are defined from the point of view of a user treating a patient with the microsurgical apparatus disclosed herein. When so treating the patient, a distal portion of the microsurgical apparatus is oriented toward the patient and a proximal portion of the microsurgical apparatus is oriented toward the user. Thus, the distal portion of a structure is the portion of the structure closest to the patient while the proximal portion of the structure is the portion of the structure closest to the user. User includes a physician or other health care professional using the microsurgical apparatus.

As used herein, computer includes a computer with one or more processors that may, in various aspects, include memory, display, mouse, keyboard, storage device(s), I/O device(s), and so forth. Computer may include, for example, single-processor or multiprocessor computers, minicomputers, mainframe computers, as well as personal computers, hand-held computing devices, mobile devices, cellular telephones, tablets, and other processor-based devices. Display includes, for example, computer screen, video display, monitor, virtual reality display, mixed reality display, and other visual interface.

Network, as used herein, includes the Internet, local area networks, cell phone networks (e.g. 4G or 5G), text messaging networks (such as MMS or SMS networks), wide area networks, and combinations thereof. Data may be communicated over the network by various wired and wireless technologies and combinations thereof. The network may include various data storage devices, input/output devices, servers, routers, amplifiers, wireless transmitters, wireless receivers, optical devices, and so forth, as would be recognized by those of ordinary skill in the art upon study of this disclosure.

An exemplary microsurgical apparatus 10 is illustrated in FIG. 1. As illustrated in FIG. 1, microsurgical apparatus 10 includes handle 20 with cable 24 in operational communication with handle 20 at handle proximal end 23. Tool package 40 with tool 70 at tool package distal end 61 is secured releasably to handle 20, with tool 70 at tool package distal end 61 including tool 70 forming distal end 15 of microsurgical apparatus 10. Distal end 15 of microsurgical apparatus 10 may be inserted into a body of a patient for diagnosis or delivery of therapy at a site within the body. In various implementations, tool 70 may include, for example, grippers for the manipulation of tissue, scissors, scalpel, or saw for the cutting of tissue including bone and soft tissue, electrodes for bipolar electrosurgery oblation and cauterization, or lumen for argon cryo-ablation.

Shaft 30 extends forth from handle distal end 21 of handle 20, as illustrated in FIG. 1. In this implementation of microsurgical apparatus 10, tool package 40 is slideably replacably received over shaft 30 to releasably lockably engage tool package proximal end 63 with handle distal end 21 of handle 20. When tool package 40 is received over shaft 30, in this implementation, tool 70 is disposed at tool package distal end 61 of tool package 40 with at least portions of tool 70 being distal of shaft distal end 31 to be viewable by image sensors 41, 43 and illuminated by light sources 42, 44 (see FIG. 2B). Tool package distal end 61 of tool package 40 is formed to expose shaft distal end 31 of shaft 30 when tool package 40 is received over shaft 30 to allow light from light sources 42, 44 to shine forth distally of tool package distal end 61 and to allow viewing of regions proximate tool package distal end 61 with image sensors 41, 43, in this implementation.

Actuator 60 is disposed near handle distal end 21 of handle 20 and near tool package proximal end 63 of tool package 40, as illustrated, when the tool package 40 is received over shaft 30, as illustrated in FIG. 1. Microsurgical apparatus 10 may be altered between first operational state 17 (see FIGS. 4A, 4C, 4E, 4G) and second operational state 19 (see FIGS. 4B, 4D, 4F, 4H) by positioning correspondingly actuator 60 between a first actuator position 101 and a second actuator position 102 that, in turn, positions tool 70 correspondingly between disengaged position 111 and engaged position 113.

As illustrated in FIG. 1, microsurgical apparatus 10 includes computer 11, network 12, external input device 13, display 14, and source 16 in communication with handle 20 via cable 24. Computer 11 is in operable communication with external input device 13, display 14, and source 16, and computer 11 is in communication with network 12, as illustrated. Data flows between computer 11, network 12, external input device 13, display 14, source 16, and cable 24 are indicated by arrows. It should be understood that computer 11 may communicate with one or more of external input device 13, display 14, source 16, and cable 24 via network 12, in certain implementations.

Cable 24, which is in operational communication with handle 20 at handle proximal end 23, may, for example, communicate electrical power, video signals, laser energy, or fluids including gasses and liquids from source 16 with handle 20 for communication with, for example, distal end 15 of microsurgical apparatus 10 via one or more pathways of cable 24, as indicated by the double arrow in FIG. 1.

Source 16 may include light source(s) such as laser(s) including laser-based femtosecond multi-color illumination, liquid source(s) such as a reservoir of distilled water or saline, a vacuum source, gas source(s) such as pressurized gas cylinder(s), mains sources of fluids including mains vacuum and mains gasses, electrical power communicated from mains electric that may be conditioned, for example, by a rectifier and/or a transformer, a vacuum source, and so forth. Source 16 configured as a light source may emit light that is, for example, coherent, tunable, of multiple wave lengths, pulsed, constant, polarized, or combinations thereof, in various implementations. Although illustrated as a single component for explanatory purposes, source 16 may include multiple components, and source 16 may be configured in various ways, as would be readily recognized by those of ordinary skill in the art upon study of this disclosure. Similarly, although illustrated as a single component for explanatory purposes, cable 24 may include multiple pathways such as fluid pathways, light pathways, electrical pathways that may be organized in various ways, as would be readily recognized by those of ordinary skill in the art upon study of this disclosure.

Computer 11 may communicate with source 16 to control, at least in part source 16 including communications of source 16 via cable 24, in this implementation. Computer 11 may control, at least in part, various operations of microsurgical apparatus 10, including, for example, illumination from light sources 42, 44 (see FIG. 2B) or electrical power communicated onto tool 70. Computer 11 may be in operable communication with various portions of microsurgical apparatus 10 including portions of tool 70, image sensors 41, 43, and light sources 42, 44 via cable 24.

External input device 13, which includes a foot pedal, joystick, or other manual input, may cooperate with computer 11 to allow the user to control, at least in part, communications of source 16 via cable 24, in this implementation. For example, external input device 13 may control the flow of electrical power from source 16 to tool 70 as directed by the user, for example, to control cauterizing using tool 70. In other implementations, external input device 13 may communicate directly with source 16.

As illustrated in FIG. 1, image sensors 41, 43 communicate with computer 11 via cable 24 to allow the user to view image 18 obtained by image sensors 41, 43 (see FIG. 2B) using display 14, which is controlled by computer 11. Image 18 may be, for example, generally continuous in real time, and image 18 may be enhanced or analyzed using various imaging technologies. Display 14 may be, for example, a display from a tablet including 3D tablets, a 3D display, or any of a variety of immersive and mixed reality computer driven heads up displays. Display 14 may provide intuitive orientation and a sense of depth to image 18, which may be important for surgery. The user may view bodily regions proximate tool 70 with image sensors 41, 43 illuminated by light sources 42, 44 using display 14 in order to navigate tool 70 at tool package distal end 61 to a site within the body or while engaging in diagnosis or the delivery of therapy at the site.

FIGS. 2A, 2B, 2C, 2D illustrates various portions of exemplary microsurgical apparatus 10 with tool package 40 removed from shaft 30. Portions of shaft 30 proximate shaft proximal end 33 are received within handle 20 to engage securely shaft 30 with handle 20, and shaft 30 extends forth from handle 20, as illustrated. Shaft 30 is rigid structurally and of constant cross-section between shaft proximal end 33 and shaft distal end 31, in this implementation. A shaft, such as shaft 30, may be flexible in other implementations. For example, shaft 30 may be between about 50 mm and about 200 mm in length, and shaft 30 may be formed of stainless steel such as ASTM 316, 420, 440 stainless steel.

Figures 2A, 2B, 2C, 2D:
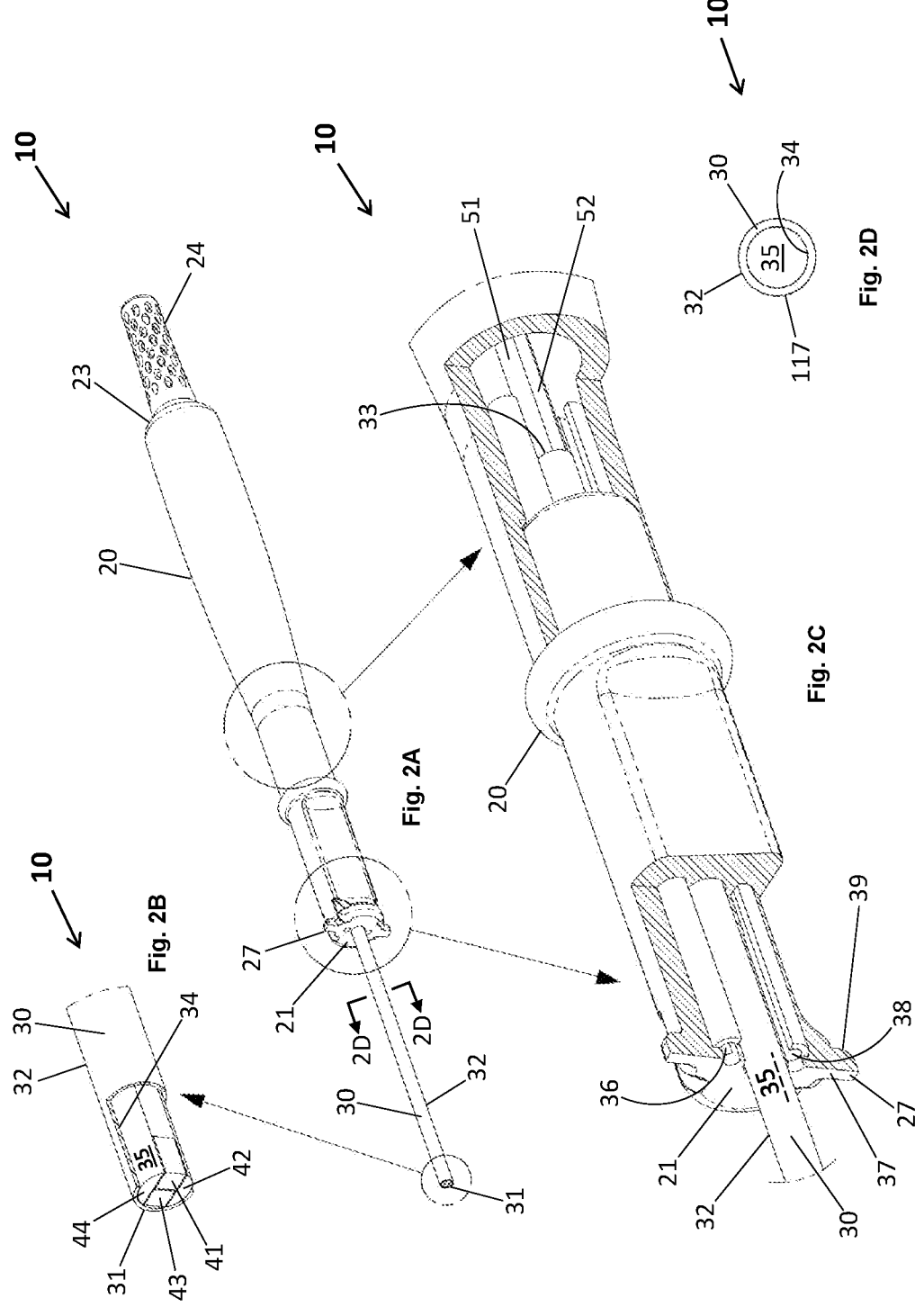
FIG. 2A illustrates by cut-away perspective view portions of the exemplary implementation of the microsurgical apparatus of FIG. 1.
FIG. 2B illustrates by cut-away perspective view portions of the exemplary implementation of the microsurgical apparatus of FIG. 1.
FIG. 2C illustrates by cut-away perspective view portions of the exemplary implementation of the microsurgical apparatus of FIG. 1.
FIG. 2D illustrates by cross-sectional view portions of the exemplary implementation of the microsurgical apparatus of FIG. 1.

As illustrated in FIG. 2D, shaft 30 has outer surface 32 and inner surface 34, and inner surface 34 defines lumen 35 passing between shaft distal end 31 and shaft proximal end 33. Shaft 30 may range in diameter including equivalent dimension(s) from about 1 mm to about 3 mm, in various implementations. Cross-section 117 of shaft 30 is generally constant between shaft proximal end 33 and shaft distal end 31, as illustrated in FIG. 2D. Although illustrated as circular, cross-section 117 may have other geometric shapes, in other implementations.

Image sensors 41, 43 are located at shaft distal end 31 to detect visual images from shaft distal end 31, and image sensors 41, 43 are oriented to view distally of shaft distal end 31, as illustrated in FIG. 2B. Image sensors 41, 43 may be, for example, video or fiberoptic, in various implementations. For example, image sensors 41, 43 may be about 2 mm in diameter including equivalent dimension(s) or less, and image sensors 41, 43 may provide about 30 to about 50 times magnification, a depth of field from about 2 mm to about 50 mm, and field of view of about 110° diagonal. For example, image sensors 41, 43 may be selected as part number OVM6946 with dimensions 1.1 mm×1.1 mm or as part number OVM6948 with dimensions 0.64 mm×0.64 mm both provided by Omni Vision, Inc. of Santa Clara, CA. Image sensors 41, 43 may communicate by image pathway 51 that passes through lumen 35, as illustrated in FIG. 2A. Image pathway 51 may include, for example, electrical cable or fiberoptic bundle operably engaged with image sensors 41, 43. Image sensors 41, 43 may communicate with computer 11 and display 14 via image pathway 51.

As illustrated in FIG. 2B, light sources 42, 44 are located at shaft distal end 31 to illuminate regions proximate shaft distal end 31. In this implementation, light sources 42, 44 are supplied by fiberoptic pathway 52 that passes through lumen 35 to communicate light to light sources 42, 44. Fiberoptic pathway 52 may be formed as a fiberoptic bundle operably engaged with light sources 42, 44, and fiberoptic pathway 52 may be in communication with source 16 or with source 16 and computer 11 via cable 24, in various implementations. Wave length(s) of the light delivered by light sources 42, 44 may be controlled by computer 11, for example, to deliver femtosecond multi-color illumination from light sources 42, 44 for spectral analysis in real time of the tissue being observed by the user. Real time femtosecond multi-color illumination driven by computer 11 combined with image processing including spectral analysis of image 18 from image sensors 41, 43 by computer 11, for example, may delineate a tumor boundary or contrast arteries and veins maybe even in micro-vessels during a procedure. Light sources 42, 44 may be formed as light emitting diodes (LED) in various implementations.

As illustrated in FIG. 2C, detent 27 is located about handle distal end 21 that lockably releasably engages detent arms 58, 59 (see FIG. 3B) on tool package 40 to secure releasably tool package 40 to handle 20. When tool package 40 is secured to handle 20, electrical pathways 36, 38 in handle 20 may communicate with electrical pathways 46, 48 in tool package 40 to flow electrical power onto tool 70. As illustrated in FIG. 2A, cable 24 is in operational communication with handle 20 at handle proximal end 23. Electrical pathways 36, 38, image pathway 51, and fiberoptic pathway 52 may extend forth from handle proximal end 23 by being incorporated within cable 24 to communicate with computer 11 and/or source 16.

Figure 3A:
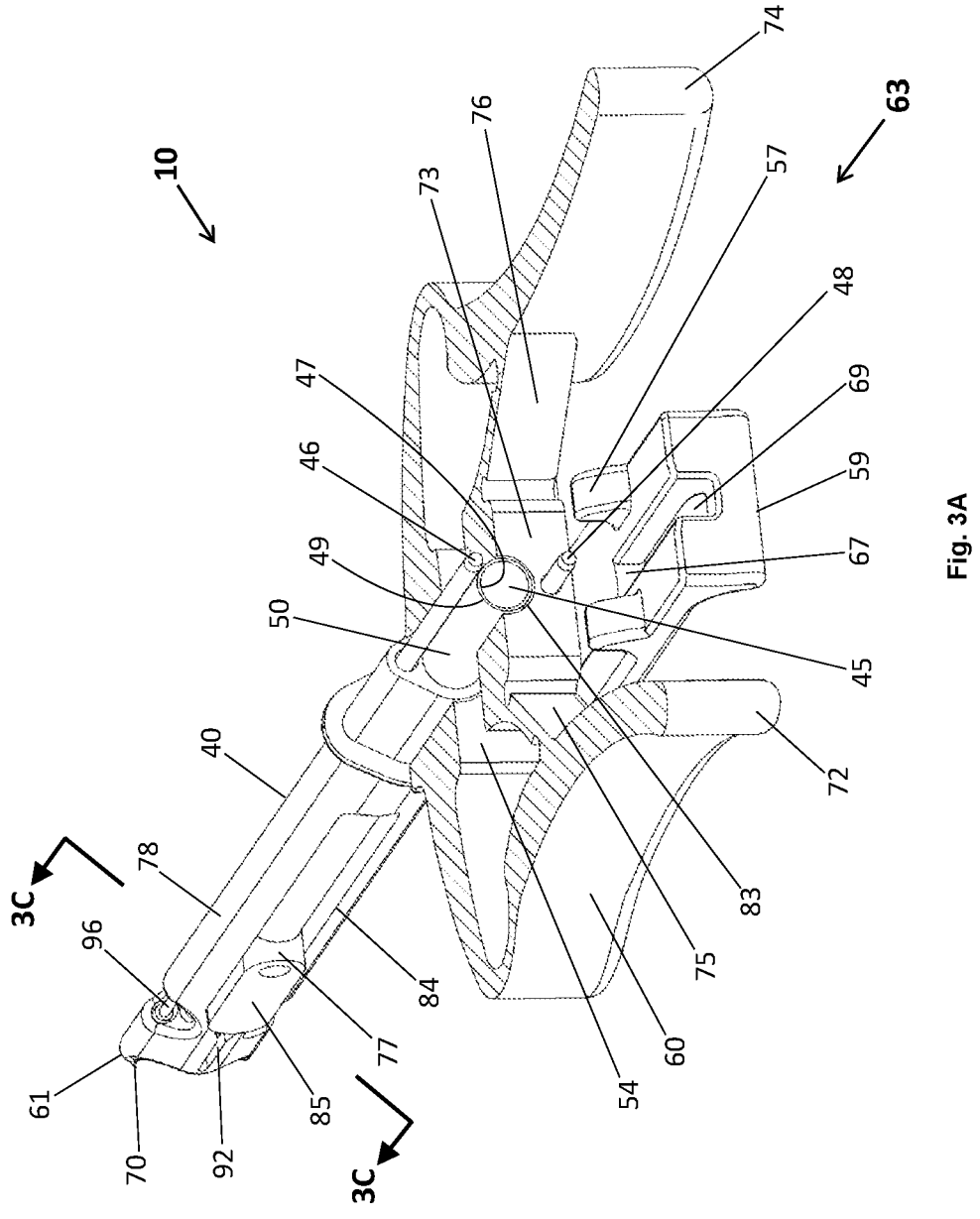
FIG. 3A illustrates by cut-away perspective view generally in a distal direction portions of the exemplary implementation of the microsurgical apparatus of FIG. 1.
Figure 3B:
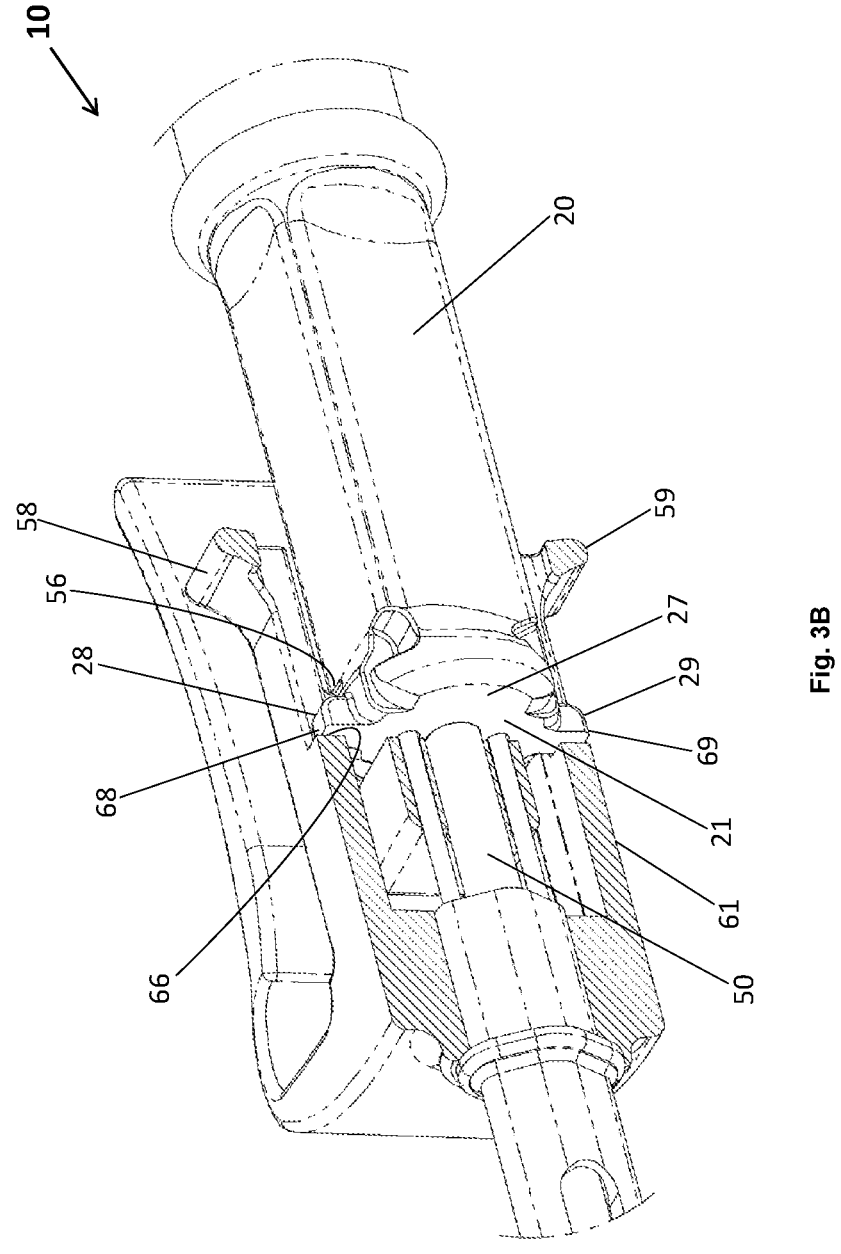
FIG. 3B illustrates by cut-away perspective view portions of the exemplary implementation of the microsurgical apparatus of FIG. 1.
Figure 3C:
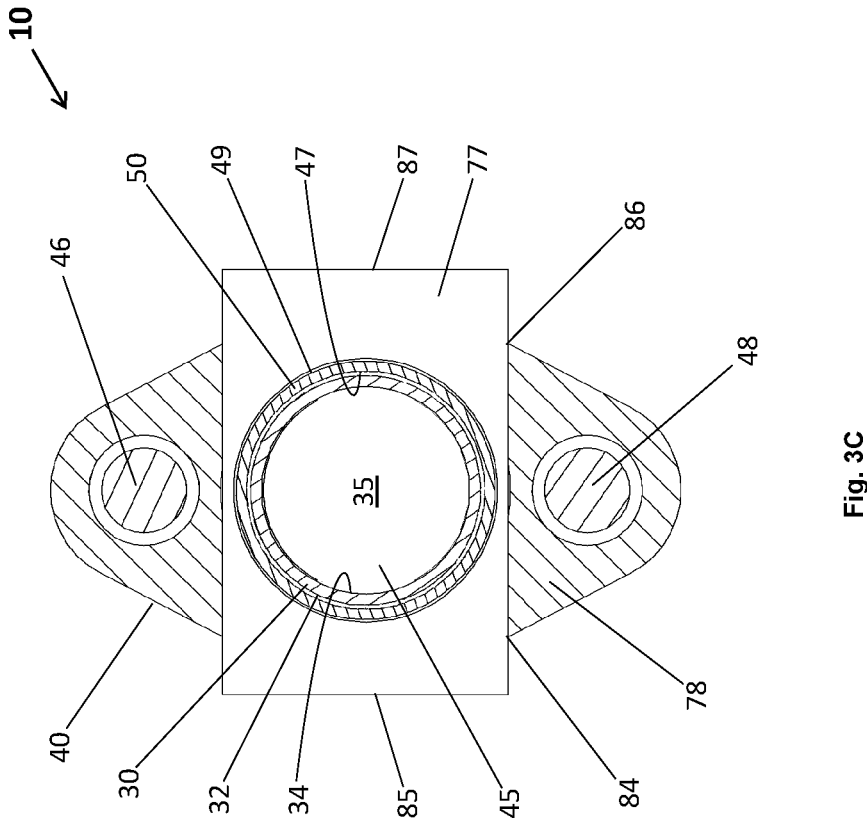
FIG. 3C illustrates by cross-sectional view portions of the exemplary implementation of the microsurgical apparatus of FIG. 1.

FIGS. 3A, 3B, 3C illustrated the releaseable engagement of tool package 40 with handle 20. As illustrated in FIG. 3A, tool package 40 includes sleeve 50 with sleeve inner surface 47 and sleeve outer surface 49, and sleeve inner surface 47 defines sleeve lumen 45. In this implementation, sleeve lumen 45 slidably receives shaft 30 that may be inserted into sleeve lumen 45 at sleeve proximal end 83, which is proximate tool package proximal end 63. Sleeve proximal end 83 is open to insertably receive shaft 30, and sleeve distal end 81 of sleeve 50 is open to expose shaft distal end 31 of shaft 30 at tool package distal end 61 when shaft 30 is received in sleeve 50.

With shaft 30 slidably received within sleeve lumen 45, detent arms 58, 59 flex to slide over projections 28, 29, respectively, of detent 27 as tool package proximal end 63 is advanced toward handle distal end 21 until projections 28, 29 align with slots 68, 69 in detent arms 58, 59, respectively, as illustrated. When projections 28, 29 align with slots 68, 69, detent arms 58, 59 relax so that projections 28, 29 are insertably received in slots 68, 69 and tool package detents 56, 57 are compressionably biased against detent proximal side 39 of detent 27 to hold detent distal side 37 including projections 28, 29 in compressionably biased engagement with slot sides 66, 67 of slots 68, 69, respectively, thus securing tool package 40 to handle 20, as illustrated in FIG. 3B.

In order to disengage tool package 40 from handle 20, tool package detents 56, 57 may be disengaged from detent 27 by flexing detent arms 58, 59 thereby disengaging slots 68, 69 from projections 28, 29 and then slidably withdrawing tool package 40 from shaft 30. Tool package proximal end 63 is withdrawn distally away from handle distal end 21 as tool package 40 is withdrawn from shaft 30. Detent arms 58, 59 may include grippable surfaces that facilitate the user's manipulation of detent arms 58, 59 in order to flex detent arms 58, 59 thereby disengaging slots 68, 69 from projections 28, 29.

As illustrated in FIG. 3A, body 73 is secured to sleeve 50 proximate sleeve proximal end 83, and actuator arms 72, 74 of actuator 60 mechanically cooperate with body 73 via struts 75, 76, respectively. Sleeve 50 is slidably received within sheath 78 so that sheath 78 overlays sleeve 50 with portions of sleeve 50 exposed in sheath slots 84, 86 formed in sheath 78, as illustrated in FIGS. 3A, 3C. Heads 85, 87 are formed as portions of headpiece 77, and headpiece 77 is affixed to sleeve 50 proximate tool package distal end 61, as illustrated in FIG. 3C. In this implementation, headpiece 77 including heads 85, 87 is formed as a unitary structure, and headpiece 77 may be affixed to sleeve 50, for example, by fastener(s), weld, or pressed fit. In other implementations, for example, heads 85, 87 may be separate elements affixed to sleeve 50 either directly or by some intermediary structure(s).

Figure 3D:
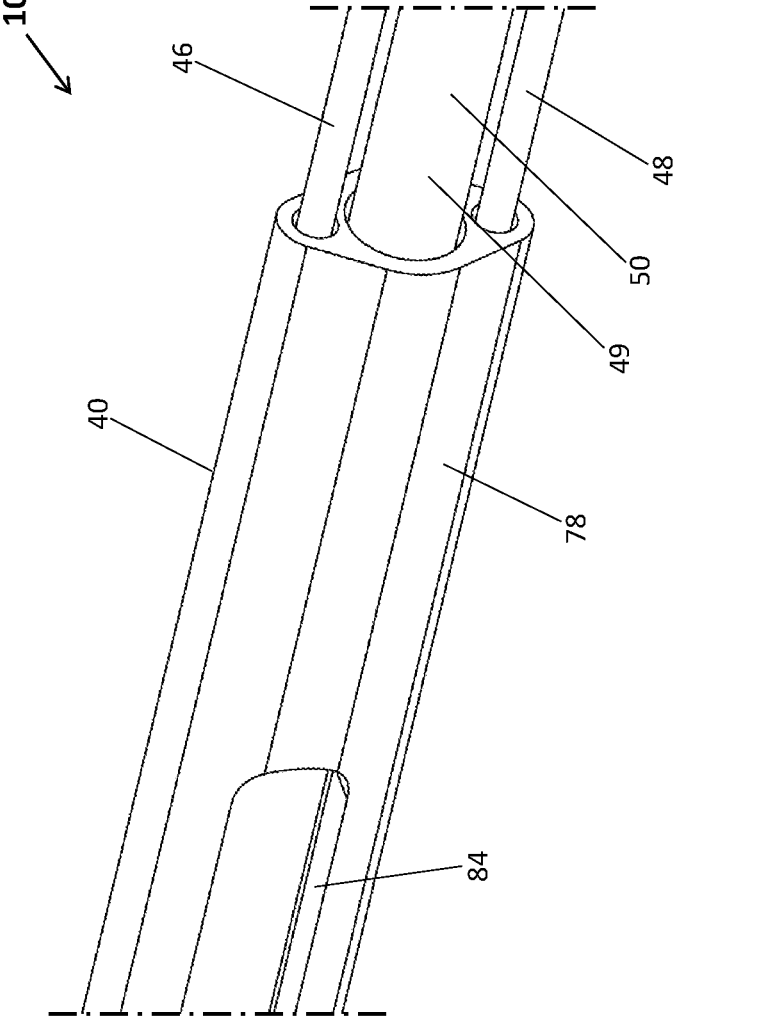
FIG. 3D illustrates by cut-away perspective view portions of the exemplary implementation of the microsurgical apparatus of FIG. 1.

Heads 85, 87 are slidably engaged with sheath 78 in sheath slots 84, 86 (also see FIGS. 4C, 4D) to prevent rotation of sleeve 50, in this implementation. Sheaths slots 84, 86 are symmetric circumferentially about sheath 78 with respect to one another, and heads 85, 87 are positioned coincident with respect to one another and opposite one another on sleeve 50 so that, for example, heads 85, 87 are positioned the same distance from sleeve proximal end 83, in this implementation. Other implementations may include various numbers of heads, such as heads 85, 87, and sheath slots, such as sheath slots 84, 86, and the heads and corresponding sheath slots may have various circumferential orientations and longitudinal orientations with respect to one another. Sheath slots 84, 86 are sized to accommodate heads 85, 87 to allow heads 85, 87 to traverse distally-proximally unimpeded within sheath slots 84, 86. Portions of sheath 78 surround sleeve 50, and electrical pathways 46, 48 pass within sheath 78, as illustrated in FIG. 3D.

Handle 20 may be formed of various hard plastics such as polyamides or polycarbonate. Actuator 60 may be formed of hard plastic with spring-like mechanical properties such as polyamides (e.g., nylon 12, 6/12), polypropylene, or polycarbonate. Sheath 78 may also be formed of plastic such as polyamides, polypropylene, or polycarbonate. Actuator 60 and sheath 78 may be formed, for example, by extrusion, injection molding, or both. Actuator 60 and sheath 78, for example, may be formed separately and joined together, or actuator 60 and sheath 78 may be formed unitarily. Portions of sheath 78 may be as thin as 25 μm between lumens, in certain implementations. In various implementations, sleeve 50 may be formed of stainless steel. Tool 70 may be formed of stainless steel such as 304 stainless steel or 316 stainless steel, and tool 70 may be coated with various coatings including metals and ceramics.

Tool package 40 may have a diameter or equivalent of about 1.5 mm and tool package 40 may generally match the length of shaft 30 being generally in the range between about 50 mm and about 200 mm in length, in certain implementations. Note that shaft 30 and/or tool package 40 may be greater than 200 mm in length in some implementations, and shaft 30 and/or tool package 40 may be less than 50 mm in length in other implementations.

Portions of microsurgical apparatus such as handle 20, shaft 30, or tool package 40 including tool 70, actuator 60, and sleeve 59 may be formed of material(s) that may be sterilized using gamma radiation. Portions of microsurgical apparatus 10 may be formed of materials that may be autoclaved or that may undergo chemical sterilization such as with ETO.

FIGS. 4A, 4C, 4E, 4G illustrate microsurgical apparatus at a first operational state 17 with actuator 60 in first actuator position 101 and, thus, tool 70 in disengaged position 111, and FIGS. 4B, 4D, 4F, 4H illustrate microsurgical apparatus 10 at a second operational state 19 with actuator 60 in second actuator position 102 and, thus, tool 70 in engaged position 113. Actuator 60 is positionable between first actuator position 101 and second actuator position 102 to correspondingly alter microsurgical apparatus between first operational state 17 and second operational state 19 in order to position tool 70 between disengaged position 111 and engaged position 113.

As illustrated in FIGS. 3A, 4C, 4D, 4G, 4H, slits 92, 93 are formed in sheath 78 distally of sheath slots 84, 86 with entries 88, 89 between slits 92, 93 and sheath slots 84, 86. Slit distal ends 107, 109 form the distal ends of slits 92, 93, respectively. Slits 92, 93 in sheath 78 near tool package distal end 61 divide sheath 78 into first component 104 that cooperates with prong 114 and second component 106 that cooperates with prong 116 with first component 104 and second component 106 connected by connecting portions 103, 105 of sheath 78, as illustrated. Prongs 114, 116 are engaged with tubular members 96, 98 that pass proximally through first component 104 and through second component 106 of tool package 40 from prongs 114, 116, respectively, in this implementation.

First component 104 and second component 106 may flex elastically including flexing elastically about connecting portions 103, 105 of sheath 78, respectively, and tubular members 96, 98 may flex to position prongs 114, 116 of tool 70 between disengaged position 111 with respect to one another and engaged position 113 with respect to one another. Prongs 114, 116 of tool 70 may be spaced apart by length 131 in disengaged position 111 and prongs 114, 116 may be spaced apart by length 133 in engaged position 113 with length 133 being less than length 131. Length 133 may be essentially nil meaning prongs 114, 116 contact one another.

Tubular members 96, 98 may communicate electrical power with prongs 114, 116, in certain implementations. Tubular members 96, 98 may either be solid or tubular members 96, 98 may form lumen that may convey fluids or contain electrical or optical pathways, in various implementations. Although illustrated as circular in cross-section, tubular members 96, 98 may have other cross-sectional geometries, in other implementations. For example, tubular members 96, 98 may be formed of metal such as steel, aluminum, or copper, or other materials such as glass or plastic.

As illustrated in FIGS. 4A, 4C, 4E, 4G, actuator 60 is in first actuator position 101 with actuator arms 72, 74 spaced apart by released length 121 and body 73 in spaced relation with face 54, at first operational state 17. Heads 85, 87 (also see FIG. 3A) are positioned at entries 88, 89 of slits 92, 93, respectively, and prongs 114, 116 of tool 70 are disengaged position 111 set apart from one another by length 131, at first operational state 17. Slits 92, 93 are generally linear of constant width that is narrower than sheath slots 84, 86 and narrower than heads 85, 87 at first operational state 17, as illustrated. Tubular members 96, 98 are undeformed and, thus, generally linear at first operational state 17, as illustrated.

As illustrated in FIGS. 4B, 4D, 4F, 4H, actuator 60 is in second actuator position 102 with actuator arms 72, 74 spaced apart by compressed length 123, and body 73 biased against face 54 at second operational state 19. Compressed length 123 is less than released length 121, in this implementation. Heads 85, 87 are positioned within slits 92, 93, respectively, and prongs 114, 116 of tool 70 are in engaged position 113 set apart from one another by length 133, at second operational state 19, with length 133 being less than length 131. Slits 92, 93 are dilated generally in V-shapes by heads 85, 87 received within slits 92, 93, respectively, with entries 88, 89 forming the entry to the V's and connecting portions 103, 105 forming the apex of the V's, as illustrated. Tubular members 96, 98 are deformed elastically at second operational state 19, as illustrated. Insertion of heads 85, 87 in slits 92, 93 deforms elastically portions of tool package 40 proximate tool package distal end 61 thereby positioning prongs 114, 116 in engaged position 113.

In order to alter microsurgical apparatus 10 from first operational state 17 to second operational state 19, the user may compress actuator arms 72, 74 together thereby positioning actuator arms 72, 74 from first actuator position 101 to second actuator position 102 thereby positioning actuator arms 72, 74 from released length 121 to compressed length 123 apart from one another. In the illustrated implementation, actuator 60 including actuator arms 72, 74 may be formed of a material that allows actuator arms to flex from released length 121 to compressed length 123 apart from one another. In other implementations, actuator arms 72, 74 hingedly rotate between released length 121 and compressed length 123.

As actuator arms 72, 74 are compressed together, actuator arms 72, 74 cooperate with struts 75, 76 and struts 75, 76, in turn, cooperate with body 73 to advance sleeve 50 distally within sheath 78 until body 73 is biased against face 54 thereby altering actuator 60 from first actuator position 101 to second actuator position 102, in this implementation. Sleeve 50 including heads 85, 87 advances distally by length Δx, as illustrated, and the biasing of body 73 against face 54 limits the distal advancement of sleeve 50 within sheath 78 to length Δx.

Figures 4A, 4B:
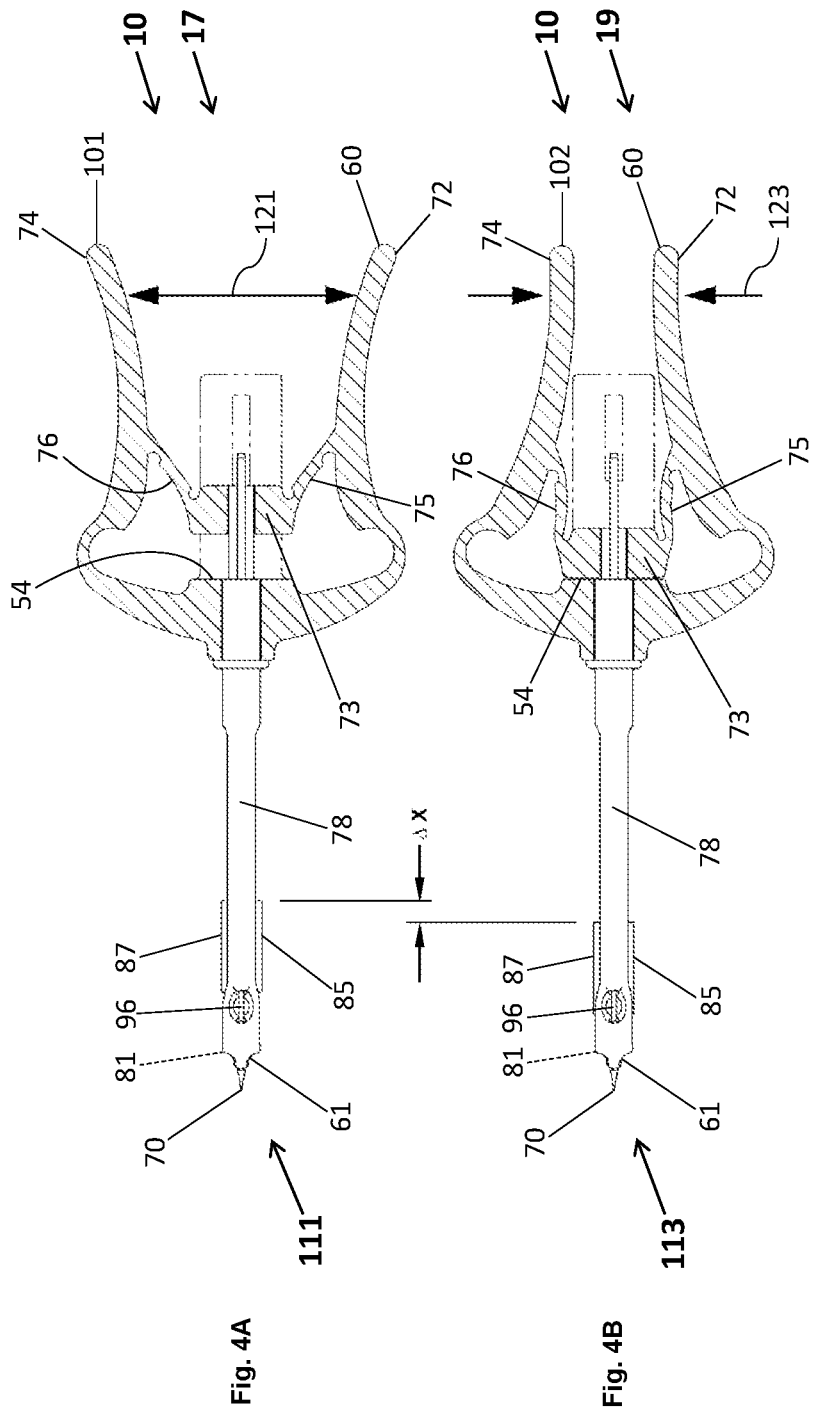
FIG. 4A illustrates by cut-away top view portions of the exemplary implementation of the microsurgical apparatus of FIG. 1 at a first operational state.
FIG. 4B illustrates by cut-away top view portions of the exemplary implementation of the microsurgical apparatus of FIG. 1 at a second operational state.
Figures 4C, 4D:
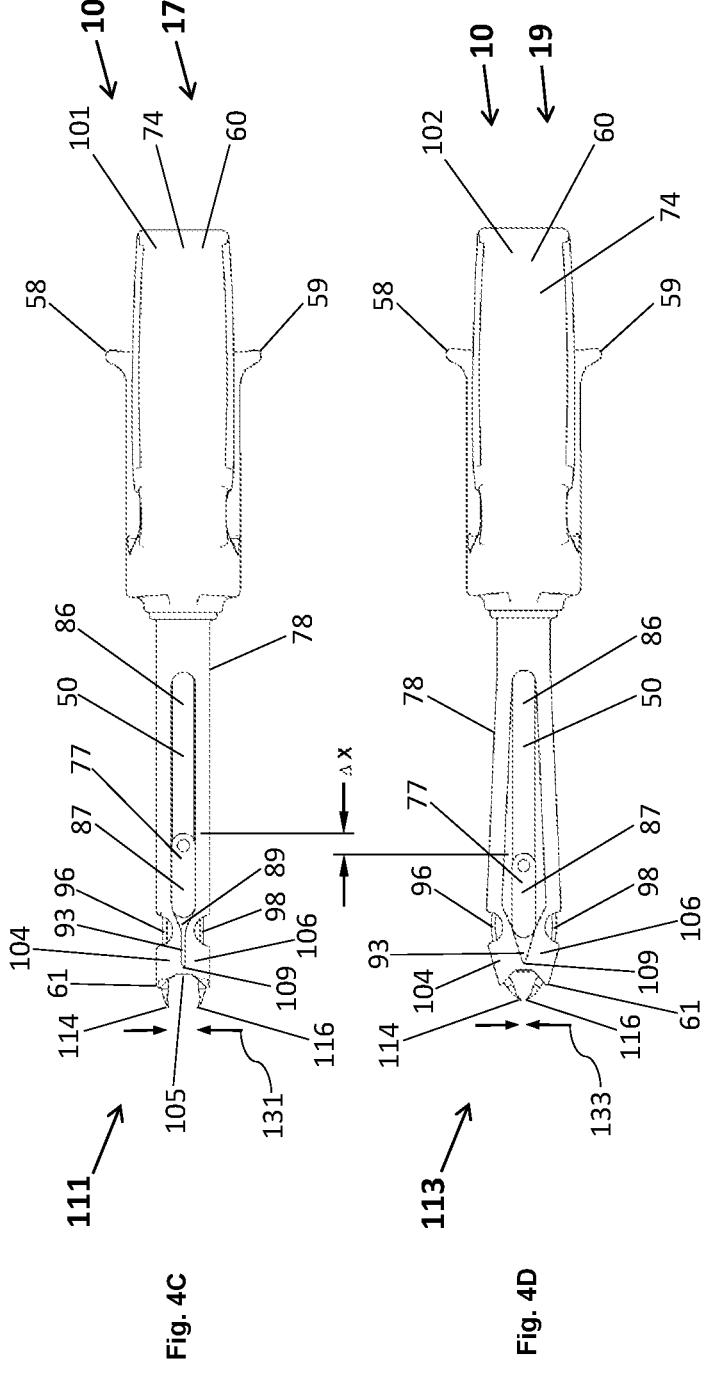
FIG. 4C illustrates by side view portions of the exemplary implementation of the microsurgical apparatus of FIG. 1 at the first operational state.
FIG. 4D illustrates by side view portions of the exemplary implementation of the microsurgical apparatus of FIG. 1 at the second operational state.
Figures 4E, 4F:
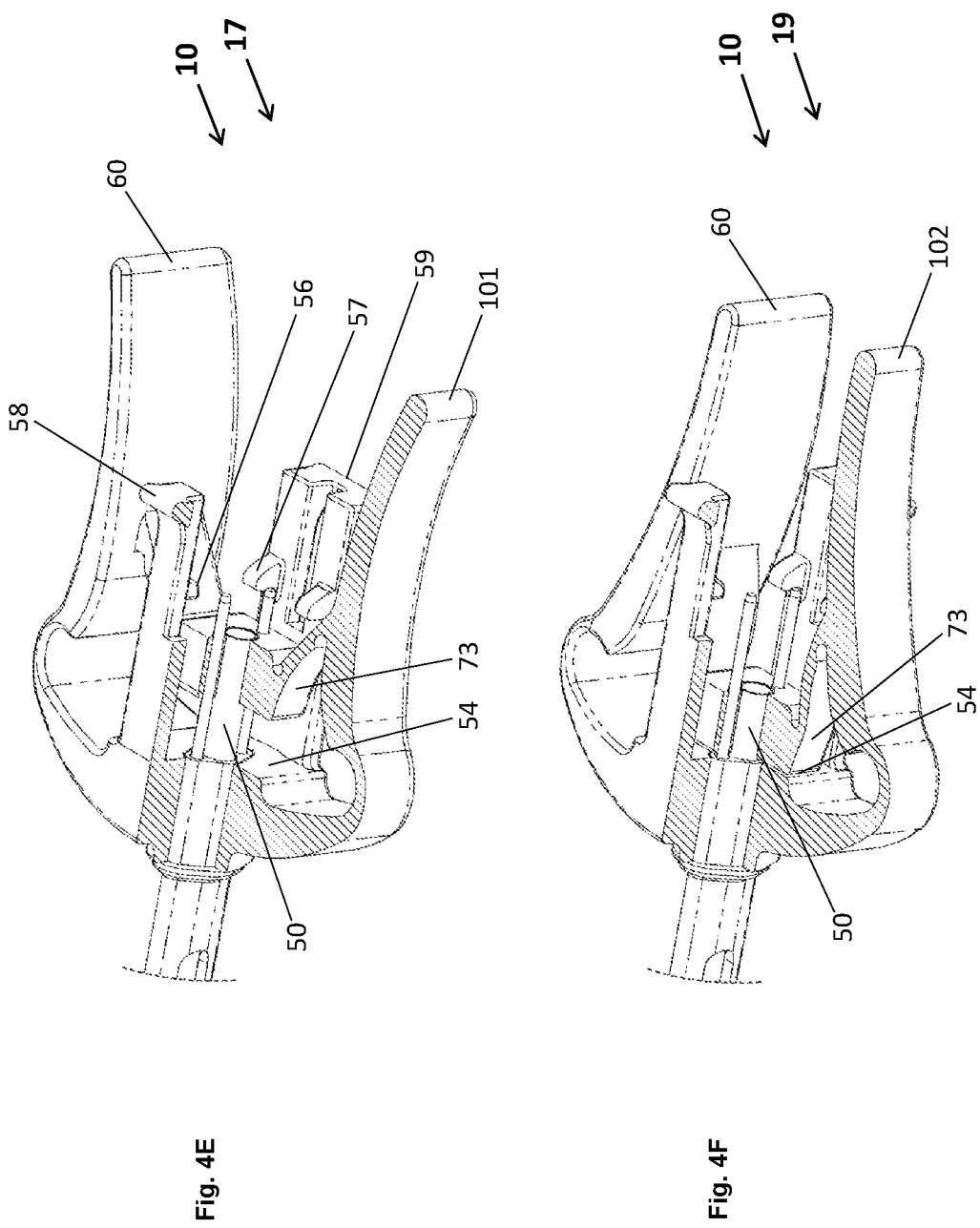
FIG. 4E illustrates by cut-away perspective view portions of the exemplary implementation of the microsurgical apparatus of FIG. 1 at the first operational state.
FIG. 4F illustrates by cut-away perspective view portions of the exemplary implementation of the microsurgical apparatus of FIG. 1 at the second operational state.
Figure 4H:
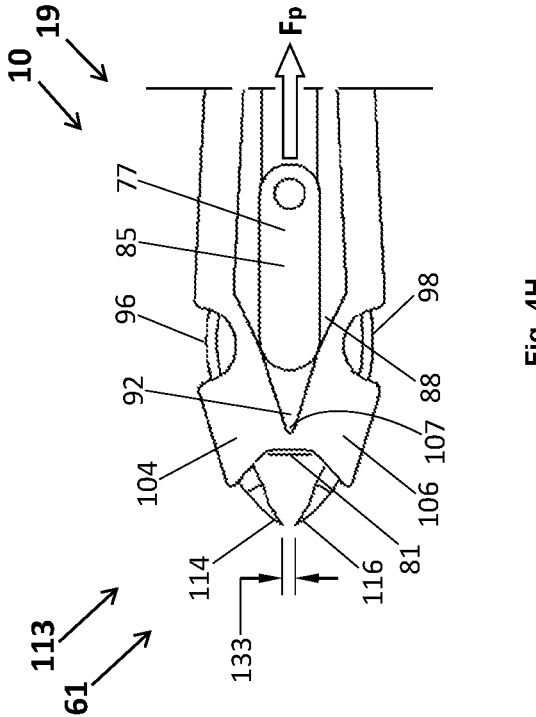
FIG. 4H illustrates by side view portions of the exemplary implementation of the microsurgical apparatus of FIG. 1 at the second operational state.
Figure 4G:
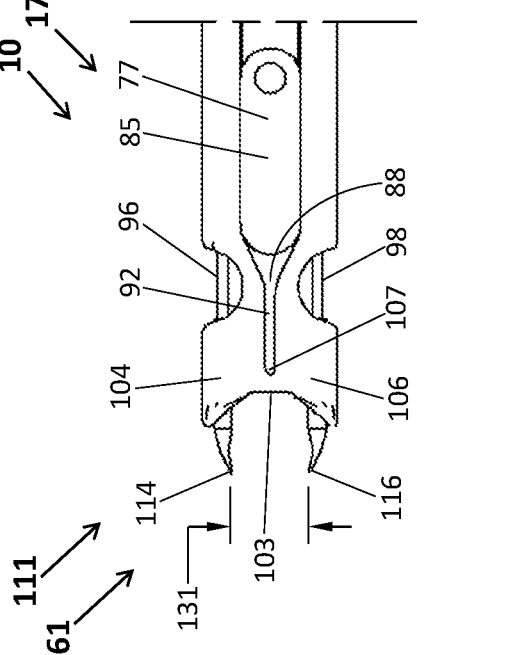
FIG. 4G illustrates by side view portions of the exemplary implementation of the microsurgical apparatus of FIG. 1 at the first operational state.

As sleeve 50 is advanced distally within sheath 78 by length Δx, heads 85, 87 are inserted into slits 92, 93 from sheath slots 84, 86 through entries 88, 89, respectively, thereby dilating slits 92, 93 from a linear shape into a V-shape, as illustrated. Sheath distal ends 107, 109 form apexes of the V-shapes. First component 104 and second component 106 of sheath 78 flex about connecting portions 103, 105 of sheath 78, respectively, to conform to the sides of the V-shape thereby positioning prongs 114, 116 from disengaged position 111 into engaged position 113 with respect to one another. The V-shape of slits 92, 93 deforms sheath 78 proximate slits 92, 93 including tubular members 96, 98, and the deformation of sheath 78 and tubular members 96, 98 produces proximal elastic force Fp in the proximal direction acting on heads 85, 87, as illustrated in FIG. 4H. Accordingly, the user must compress actuator arms 72, 74 with force sufficient to overcome proximal elastic force Fp in order to maintain actuator 60 in second actuator position 102, and, thus, maintain microsurgical apparatus 10 at second operational state 19 with prongs 114, 116 of tool 70 in engaged position 113.

In order to alter microsurgical apparatus 10 from second operational state 19 to first operational state 17, the user may release the compression of actuator arms 72, 74. When the user releases the compression of actuator arms 72, 74 with actuator 60 in second actuator position 102, and, thus, microsurgical apparatus 10 in second operational state 19, materials in sheath 78 proximate slits 92, 93 that are deformed by dilation of slits 92, 93 and tubular members 96, 98 that are elastically deformed rebound expelling heads 85, 87 proximally through entries 88, 89 back into sheath slots 84, 86, respectively, thereby releasing proximal elastic force Fp as slits 92, 93 revert from being V-shaped to being linearly shaped and tubular members 96, 98 revert to linear shape. As heads 85, 87 are expelled proximally from slits 92, 93 into sheath slots 84, 86 through entries 88, 89, respectively, sleeve 50 is forcibly withdrawn proximally disengaging body 73 from biased engagement with face 54 to spaced relation with face 54. Sleeve 50 including heads 85, 87 withdraws proximally by length Δx, as illustrated. As body 73 is disengaged from biased engagement with face 54, body 73 cooperates with struts 75, 76 that, in turn, cooperate with actuator arms 72, 74 to position actuator 60 in first actuator position 101 with actuator arms at released length 121 with respect to one another thereby returning microsurgical apparatus 10 back to first operational state 17 from second operational state 19 and prongs 114, 116 of tool 70 from engaged position 113 to disengaged position 111.

An exemplary microsurgical apparatus 200 is illustrated in FIGS. 5A, 5B, 5C, 5D, 5E, 5F, 5G, 5H. As illustrated in FIGS. 5A, 5B, 5C, 5D, 5E, 5F, 5G, 5H, tool package 240, with tool 270 at tool package distal end 261, is secured releasably to handle 220 of exemplary microsurgical apparatus 200. Sleeve 250 of tool package 240 is slideably received over shaft 230 and tool package proximal end 263 of tool package 240 releasably lockably engages handle distal end 221 of handle 220, as illustrated. Heads 285, 287 are unitary portions of headpiece 277 that is affixed to sleeve 250 distally, body 273 is secured to sleeve 250 proximally, and sheath 278 overlays portions of sleeve 250, as illustrated.

Figure 5A:
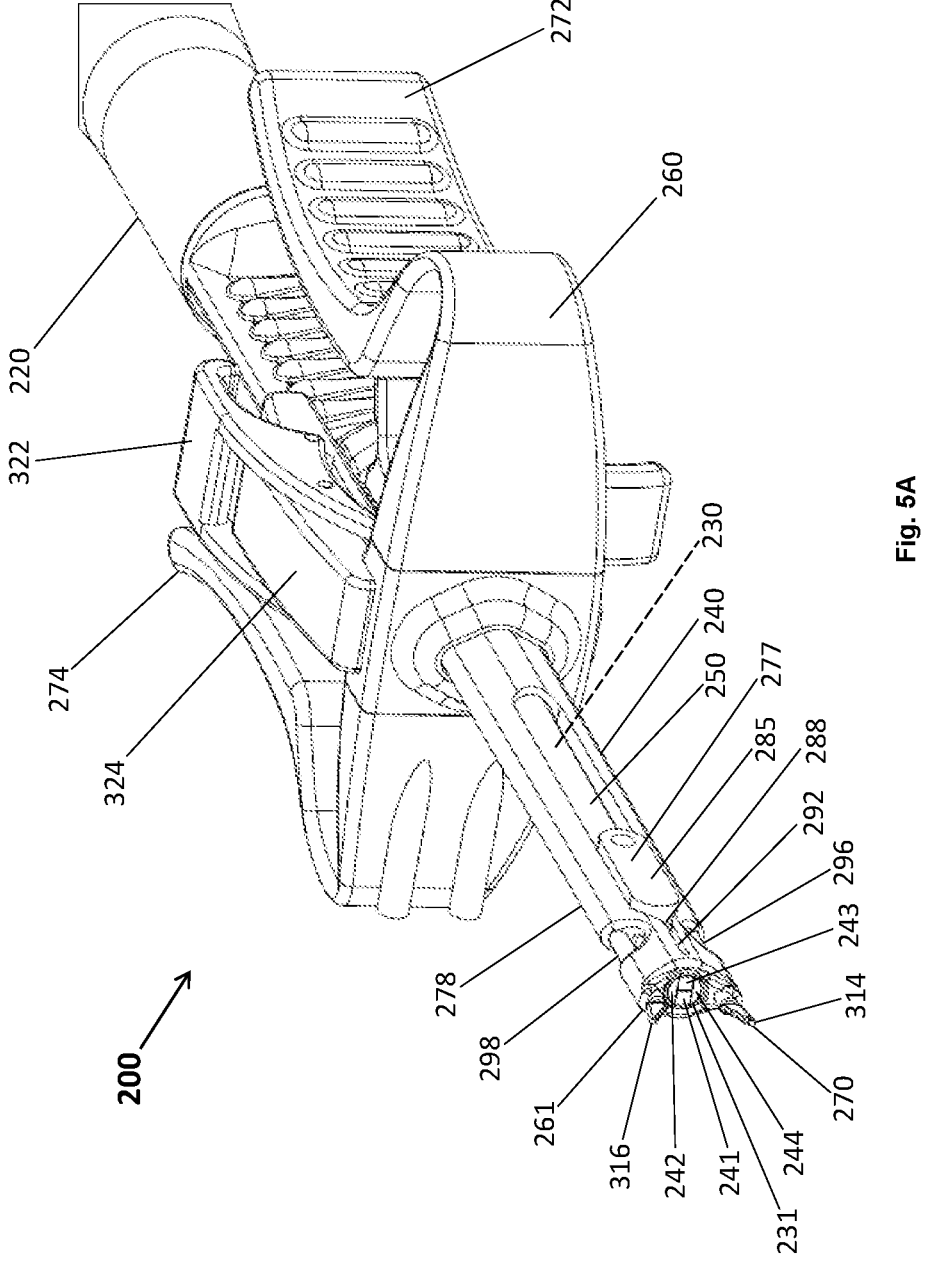
FIG. 5A illustrates by perspective view a second exemplary implementation of a microsurgical apparatus.
Figures 5B, 5C:
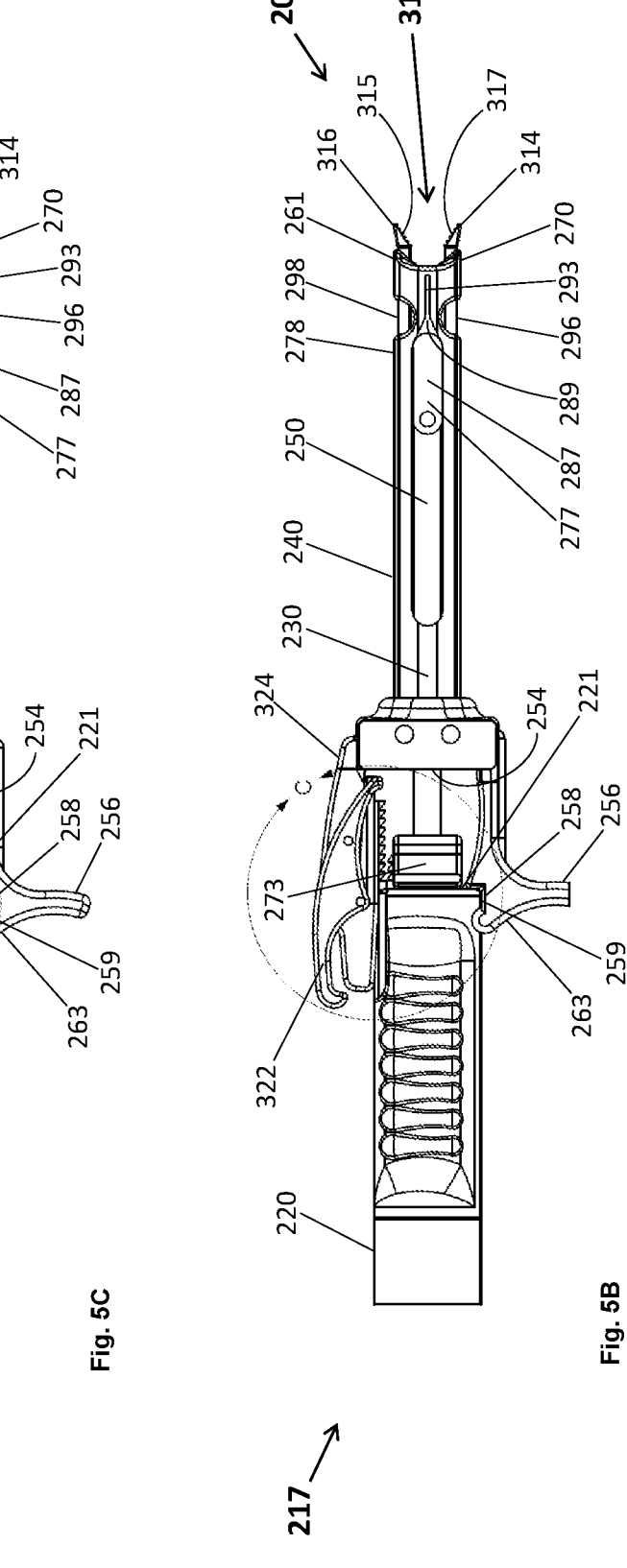
FIG. 5B illustrates by side view portions of the exemplary implementation of the microsurgical apparatus of FIG. 5A at a first operational state.
FIG. 5C illustrates by side view portions of the exemplary implementation of the microsurgical apparatus of FIG. 5A at a second operational state.

As illustrated in FIGS. 5B, 5C, tool package arm 256 of tool package 240 includes tool package detent 258 formed as a channel that releasably engages detent 259 formed as a spline in handle 220 by flexure of tool package arm 256 as tool package proximal end 263 of tool package 240 is slid toward handle distal end 221 of handle 220 by insertion of shaft 230 into sleeve 250. The user may flex tool package arm 256 to release the engagement between tool package detent 258 and detent 259 and then remove tool package slidingly from shaft 230, in this implementation. Also, the user may, for example, manipulate tool 270 by tool package arm 256 during usage of microsurgical apparatus 200.

In this implementation, tool 270 includes jaws 314, 316 with gripping surfaces 315, 317, respectively, that allow jaws 314, 316, for example, to grasp tissues. Gripping surfaces 315, 317 may include teeth, texture, roughness elements, and so forth. Jaws 314, 316 cooperate with tubular members 296, 298, respectively, as illustrated, and tubular members 296, 298 may, for example, communicate fluids, electrical power, or heat with jaws 314, 316.

Light sources 242, 244 and image sensors 241, 243 are disposed at shaft distal end 231 of shaft 230, as illustrated. When tool package 240 is received over shaft 230, in this implementation, tool 270 is disposed at tool package distal end 261 of tool package 240 with at least portions of tool 270 being distal of shaft distal end 231 in order to be illuminated by light sources 242, 244 and to be viewable by image sensors 241, 243 when tool 270 is employed, as illustrated.

Actuator 260 with actuator arms 272, 274 is disposed proximate tool package proximal end 263 of tool package 240, and actuator 260 is located proximate handle distal end 221 of handle 220 when tool package 240 is received over shaft 230, as illustrated in FIG. 5A. Shaft distal end 231 of shaft 230 includes light sources 242, 244 and image sensors 241, 243, in this implementation. Tool package distal end 261 of tool package 240 is formed to expose shaft distal end 231 of shaft 230 when tool package 240 is received over shaft 230 to allow light from light sources 242, 244 to shine forth distally of tool package distal end 261 and to allow viewing of regions distal of tool package distal end 261 with image sensors 241, 243, as illustrated in FIG. 5A.

Microsurgical apparatus 200 may be altered between first operational state 217 (see FIGS. 5B, 5D) and second operational state 219 (see FIGS. 5C, 5E) to position tool 270 between disengaged position 311 and engaged position 313, respectively. Actuator 260 of microsurgical apparatus 200 cooperates with body 273 and body cooperates with sleeve 250 generally in accordance with the cooperation of actuator 60 with body 73 and sleeve 50 of microsurgical apparatus 10 to position tool 270 between disengaged position 311 illustrated in FIG. 5B and engaged position 313 illustrated in FIG. 5C. Note that actuator 260 is omitted from FIGS. 5B, 5C, 5D, 5E, 5F for purposes of clarity of explanation.

As illustrated in FIG. 5B, body 273 in spaced relation with face 254 in first operational state 217. Heads 285, 287 are positioned at entries 288, 289 of slits 292, 293, respectively, and jaws 314, 316 of tool 270 are disengaged position 311 apart from one another, at first operational state 217. Slits 292, 293 are generally linear of constant width, tubular members 296, 298 are linear longitudinally, and sheath 278 is not elastically deformed by heads 285, 287 at first operational state, as illustrated.

As illustrated in FIG. 5C, compression of actuator arms 272, 274 of actuator 260 (omitted from FIG. 5C) advances body 273 distally thereby advancing sleeve 250, to which body 273 is secured, until body 273 is biased against face 254 at second operational state 219. Toothed engagement of teeth 331 of body 273 and lock teeth 333 of lock member 324 act as a ratchet that allows body 273 and sleeve 250 to advance distally while preventing proximal motion of body 273 and sleeve 250, as illustrated in FIG. 5E.

Jaws 314, 316 cooperate with sheath 278 and with tubular members 296, 298 to close or open as heads 285, 287 are inserted into or withdrawn from slits 292, 293, respectively, by distal advancement or proximal withdrawal of sleeve 250, respectively. As body 273 is advanced distally by actuator 260, sleeve 250 is advanced distally thereby inserting heads 285, 287 into slits 292, 293, respectively to splay slits 292, 293 apart thereby progressively closing jaws 314, 316 of tool 270 from disengaged position 311 toward engaged position 313. Slits 292, 293 are progressively deformed elastically generally in V-shapes and tubular members 296, 298 are progressively deformed elastically from the linear as heads 285, 287 are progressively inserted into slits 292, 293, respectively, thereby positioning jaws 314, 316 from disengaged position 311 toward engaged position 313 with respect to one another. When body 273 is biased against face 254, jaws 314, 316 are in engaged position 313 and microsurgical apparatus is in second operational state 219, as illustrated in FIG. 5C.

Figure 5D:
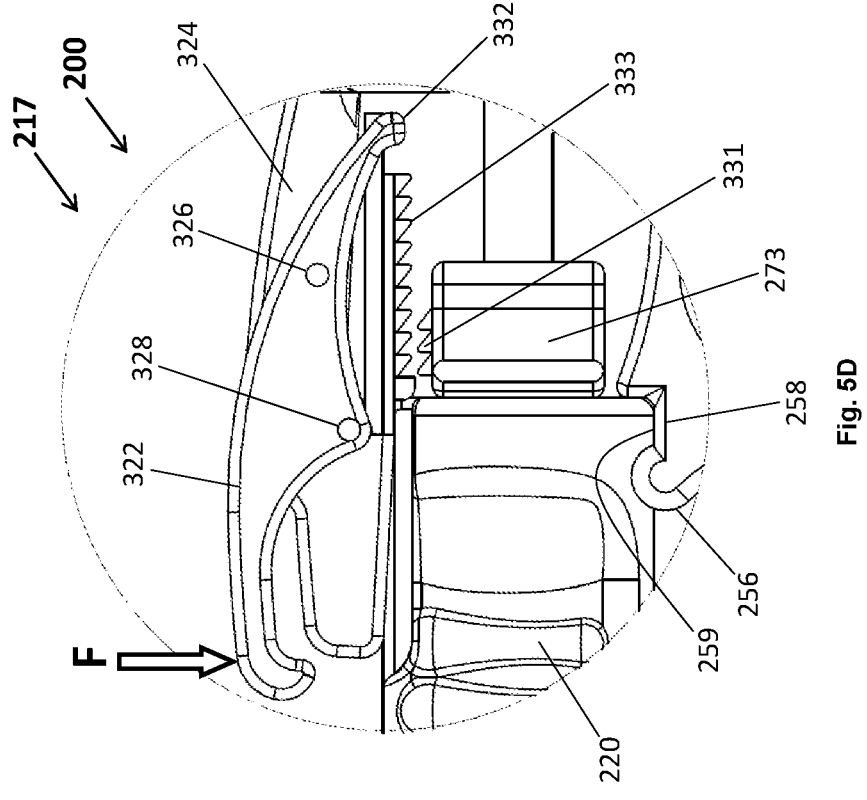
FIG. 5D illustrates by side view portions of the exemplary implementation of the microsurgical apparatus of FIG. 5A at the first operational state.
Figure 5E:
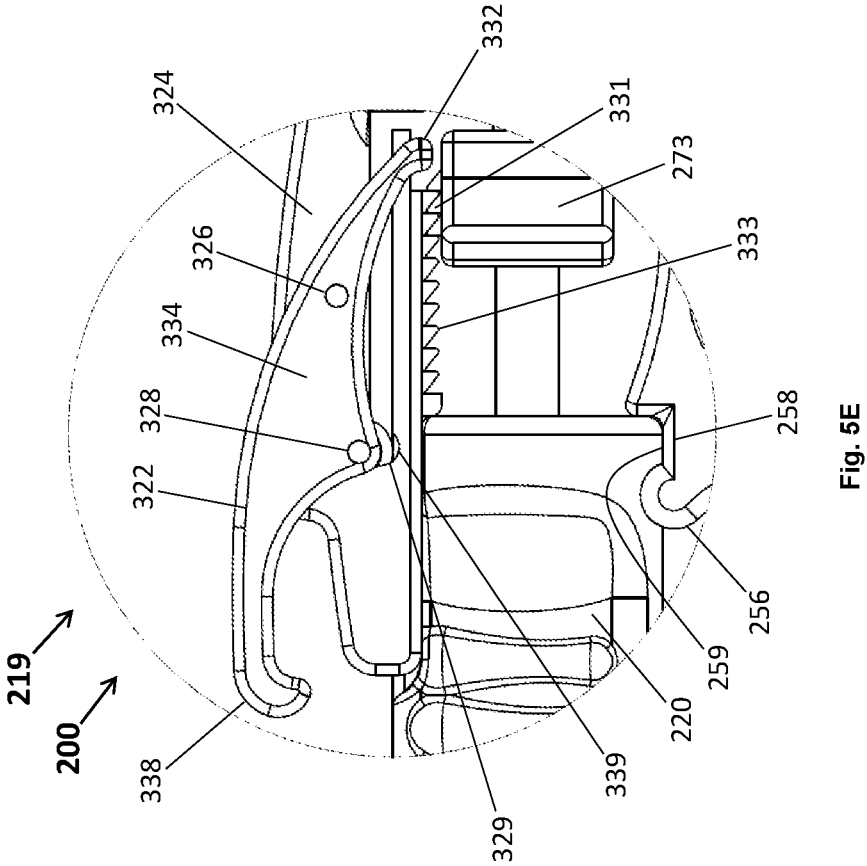
FIG. 5E illustrates by side view portions of the exemplary implementation of the microsurgical apparatus of FIG. 5A at the second operational state.
Figure 5F:
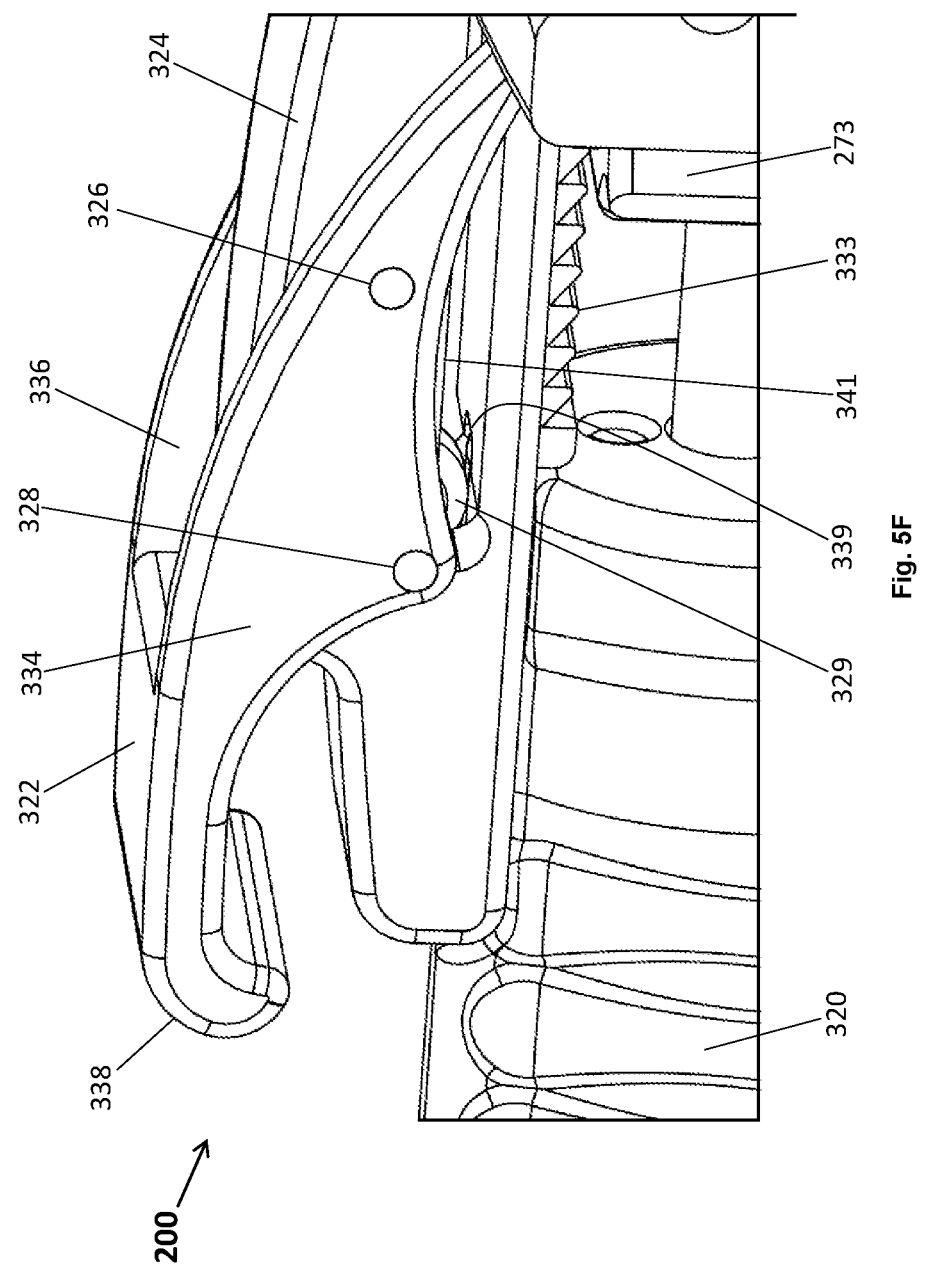
FIG. 5F illustrates by perspective view portions of the exemplary implementation of the microsurgical apparatus of FIG. 5A.
Figure 5G:
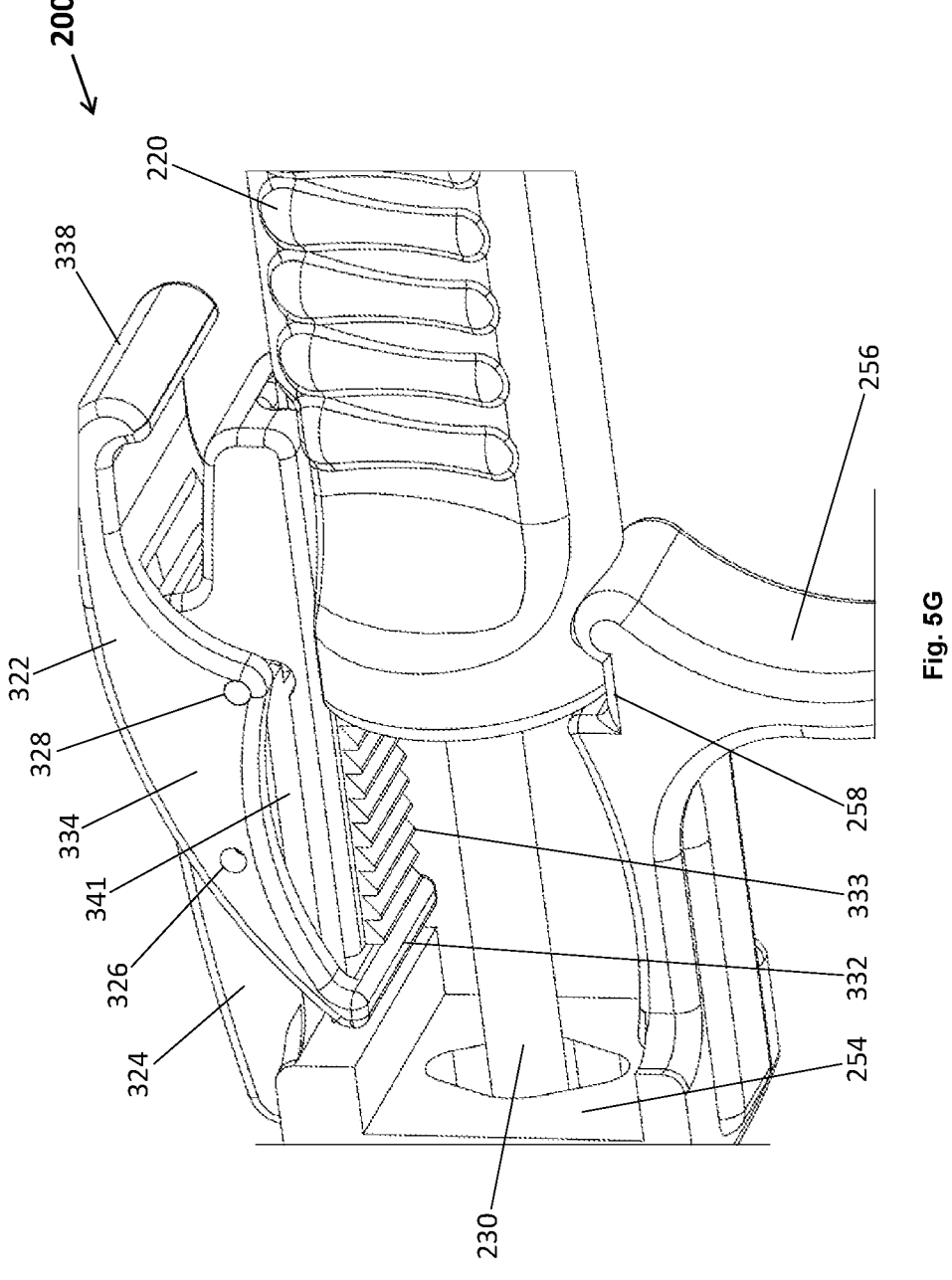
FIG. 5G illustrates by perspective view portions of the exemplary implementation of the microsurgical apparatus of FIG. 5A.
Figure 5H:
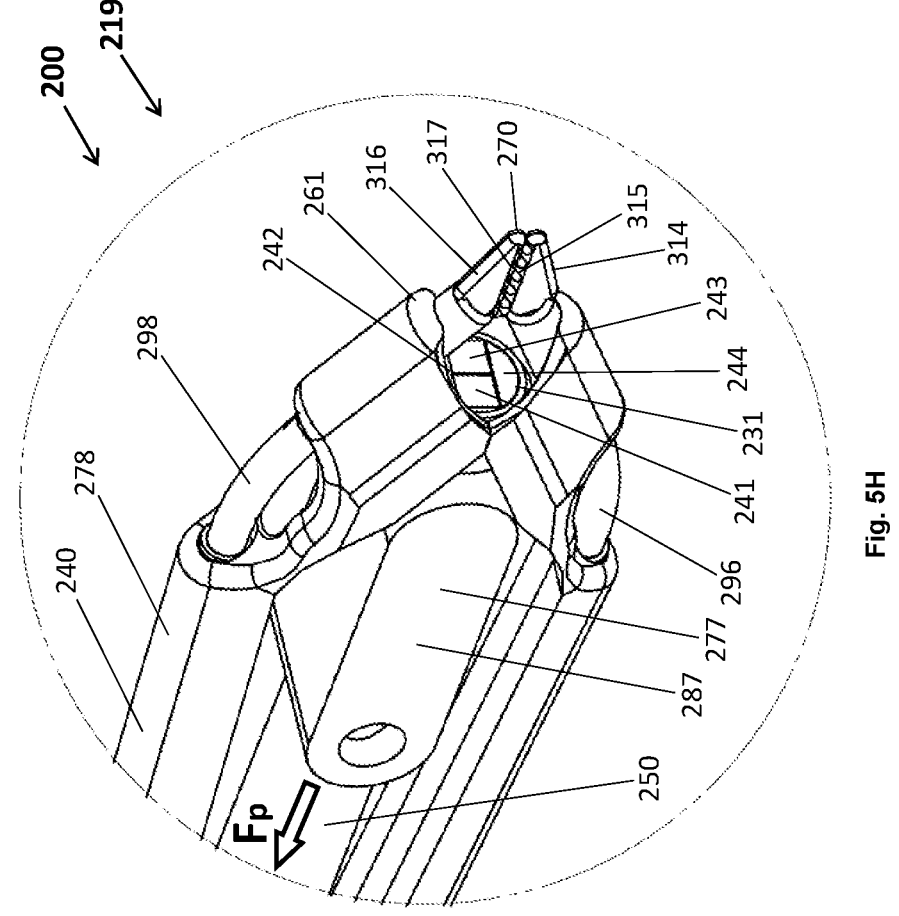
FIG. 5H illustrates by perspective view portions of the exemplary implementation of the microsurgical apparatus of FIG. 5A at the second operational state.

The elastic deformation of the material of sheath 278 and tubular members 296, 298 by the progressive insertion of heads 285, 287 into slits 292, 293 creates proximal elastic force Fp on heads 285, 287, as illustrated in FIG. 5H. Teeth 331 of body 273 and lock teeth 333 of lock member 324 are oriented to act as a ratchet that allows progressive distal insertion of heads 285, 287 into slits 292, 293 while preventing proximal motion of body 273 from proximal elastic force Fp, in this implementation. That is, the ratchet between teeth 331 and lock teeth 333 prevents proximal elastic force Fp from expelling sleeve 250 and body 273 in the proximal direction, in this implementation. Jaws 314, 316 may be held at disengaged position 311, engaged position 313, or positions between disengaged position 311 and engaged position 313 by the toothed engagement of teeth 331 of body 273 with lock teeth 333 of lock member 324 without the user compressing actuator arms 272, 274 of actuator 260. The available positions between disengaged position 311 and engaged position 313 at which jaws 314, 316 may be held may be determined by the density of teeth 331 of body 273 and lock teeth 333 of lock member 324.

Release of the compression of actuator arms 272, 274 along with release of the toothed engagement of teeth 331 of body 273 and lock teeth 333 of lock member 324 allows proximal elastic force Fp to expel heads 285, 287 from slits 292, 293 thus withdrawing sleeve 250 and body 273 in the proximal direction thereby altering microsurgical apparatus 200 from second operational state 219 with tool 270 in engaged position 313 to first operational state 217 with tool 270 in disengaged position 313.

As illustrated in FIGS. 5D, 5E, 5F, lock member 324 is planar with distal-proximal orientation, and release member 322 includes release member arms 334, 336 in gapped disposition and parallel with portions of lock member 324. Release member arms 334, 336 are joined to one another by grip member 338 located generally proximal of release member arms 334, 336, by pin 326 that passes between release member arms 334, 336 through lock member 324 to pivotably connect release member arms 334, 336 with lock member 324, and by cross member 332 that passes between release member arms 334, 336 proximate distal portions of lock teeth 333. Wheel 329 is rotatably engaged with axle 328 that passes between release member arms 334, 336 through opening 341 in lock member 324, and wheel 329 is received in notch 339 in lock member 324 within opening 341, as illustrated in FIG. 5F. As illustrated in FIG. 5G, cross member 332 passes between release member arms 334, 336 proximate distal portions of lock teeth 333. Opening 341 is also illustrated in FIG. 5G.

As indicated in FIG. 5D, the user may apply force F to grip member 338 that rotates release member 322 counter-clockwise about axle 328 thereby applying forces opposite force F to lock member 324 at pin 326 and at cross member 332. Grip member 338 may include grippable features that facilitate manipulation by the user. The forces applied to lock member 324 at pin 326 and at cross member 332 causes lock member 324 to flex elastically thereby releasing lock teeth 333 from toothed engagement with teeth 331 allowing body 273 and attached sleeve 250 to withdraw proximally propelled by proximal elastic force Fp. Proximal elastic force Fp expels heads 285, 287 proximally as slits 292, 293 revert from being V-shaped to being linearly shaped thereby relieving elastic tensions in material surrounding slits 292, 293 and tubular members 296, 298 revert from being curved to being linear longitudinally. As heads 285, 287 are expelled proximally from slits 292, 293, body 273 and sleeve 250 withdraw in the proximal direction placing jaws 314, 316, in disengaged position 311.

Figures 6A, 6B:
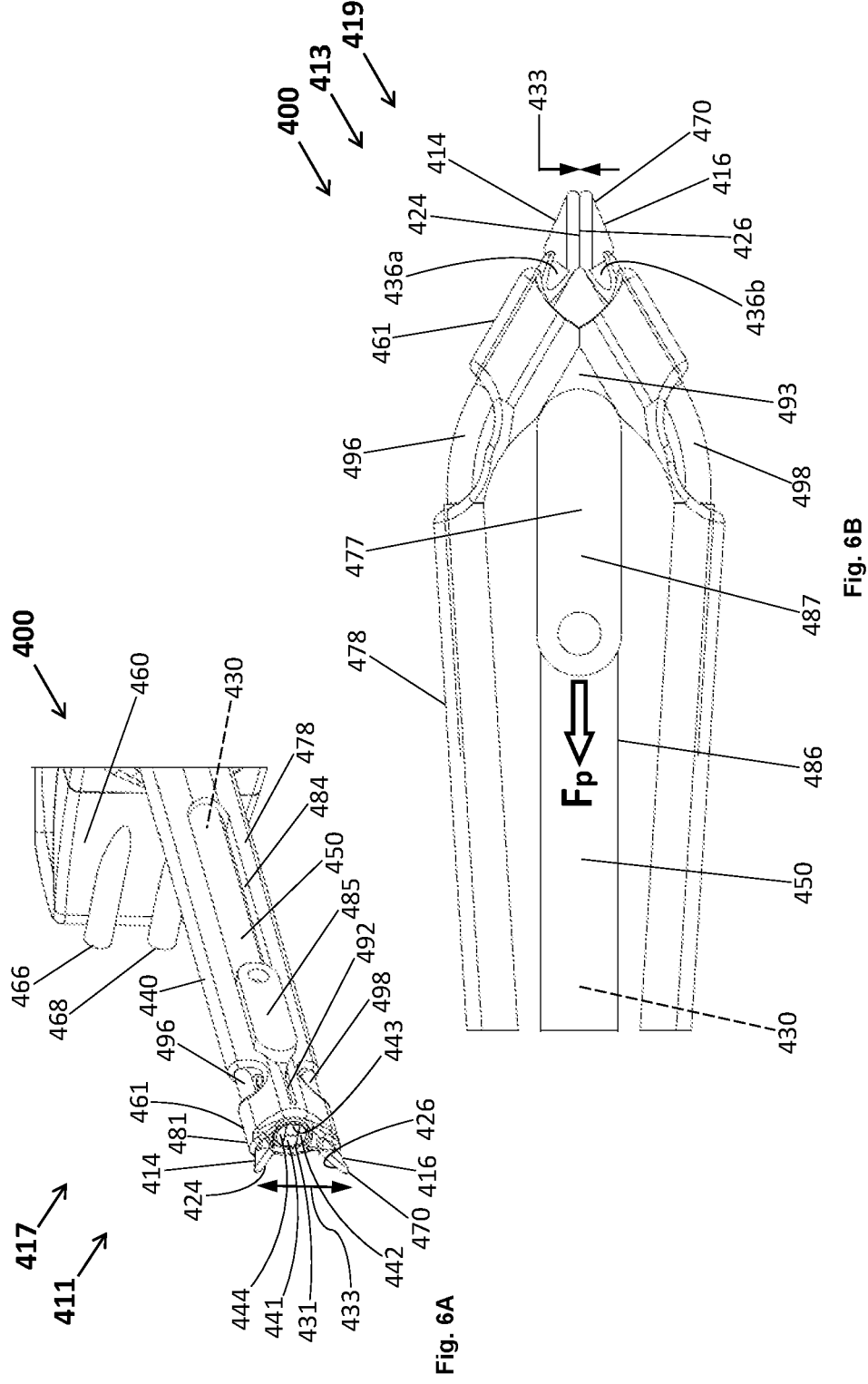
FIG. 6A illustrates by perspective view portions of a third exemplary implementation of a microsurgical apparatus at a first operational state.
FIG. 6B illustrates by side view portions the exemplary implementation of the microsurgical apparatus of FIG. 6A at a second operational state.

FIGS. 6A and 6B illustrate portions of exemplary micro-surgical apparatus 400. As illustrated in FIG. 6A, shaft 430 is insertably removably received within sleeve 450 of tool package 440 to engage releaseably tool package 440 with a handle, such as handle 20, 220. As illustrated in FIGS. 6A and 6B, tool package 440 includes tool 470 at tool package distal end 461. Tool 470 includes blades 414, 416 with edges 424, 426, respectively, and tool 470 includes nozzles 436a, 436b, as illustrated. Blades 414, 416 cooperate with tubular members 496, 498 that pass proximally within tool package 440 from blades 414, 416. Images sensors 441, 443 in combination with lights sources 442, 444 located at shaft distal end 431 of shaft 430 allow the user, for example, to view bodily regions generally distal of tool package distal end 461, and tool package distal end 461 is formed to expose image sensors 441, 443 and light sources 442, 444 when tool package 440 is received over shaft 430.

Tubular members 496, 498 form lumen for fluid communication between ports 466, 468 positioned on actuator 460 and nozzles 436a, 436b, in this implementation, and other fluid pathways may be provided in tool package 470 for fluid communication between ports 466, 468 and tubular members 496, 498. For example, fluid, such as saline solution, may be input into ports 466, 468 and communicated to nozzles 436a, 436b for discharge through nozzles 436a, 436b at least in part via tubular members 496, 498, respectively. Fluid may be discharged through nozzles 436a, 436b to remove debris resulting from cutting by blades 414, 416. Suction may be applied at one or both of ports 466, 468 to withdraw material through nozzles 436a, 436b. Fluid, for example, may be input into port 466 and withdrawn from port 468 to discharge fluid through nozzle 436a and simultaneously withdraw fluid through nozzle 436b. Various fluid sources, such as source 16, fluid pathways such as hoses, tubing, pipes, as well as couplings, and so forth may be provided to communicate fluid(s) with ports 466, 468, as would be readily recognized by those of ordinary skill in the art upon study of this disclosure.

As illustrated in FIG. 6A, heads 485, 487 are formed as portions of headpiece 477 as a unitary structure that is affixed to sleeve 450. Heads 485, 487 are positioned within sheath slots 484, 486 of sheath 478, respectively, when blades 414, 416 are in disengaged position 411, in this implementation. Blades 414, 416 cooperate with sheath 478 and with tubular members 496, 498 to diminish length 433 between blades 414, 416 as heads 485, 487 are inserted into slits 492, 493 from sheath slots 484, 486, respectively, by distal advancement of sleeve 450 thereby positioning blades 414, 416 in engaged position 413 illustrated in FIG. 6B. Insertion of heads 485, 487 into slits 492, 493, respectively, creates proximal force Fp in the proximal direction on heads 485, 487, and, thus, on sleeve 450. Absent an opposing force such as from the ratchet of teeth 331 and lock teeth 333 of microsurgical apparatus 200, compression of actuator arms 72, 74 of microsurgical apparatus 10, or compression of actuator arms 272, 274 of microsurgical apparatus 200, proximal force Fp expels heads 485, 487 from slits 496, 498 back into sheath slots 484, 486, and, thus, withdraws sleeve 450 in the proximal direction to position blades 414, 416 from engaged position 413 to disengaged position 411. Length 433 between blades 414, 416 increases as heads 485, 487 are expelled proximally from slits 492, 493 into sheath slots 484, 486, respectively, and sleeve 450 withdraws proximally thus positioning blades 414, 416 from engaged position 413 to disengaged position 411. Sleeve 450 may be advanced distally and withdrawn proximally to position blades 414, 416 between engaged position 413 at second operational state 419 of microsurgical apparatus 400 and disengaged position 411 at first operational state 417 of microsurgical apparatus 400, respectively, generally in the same manner as in exemplary microsurgical apparatus 10, 200.

Edges 424, 426 are sharpened for cutting, and positioning blades 414, 416 between disengaged position 411 and engaged position 413 causes blades 414, 416 to cut in a scissor like manner, in this implementation. Blades 414, 416 may slide against each other in a scissor-like manner, at least in part, as blades are positioned between engaged position 413 and disengaged position 411. As illustrated in FIG. 6A, images sensors 441, 443 in combination with lights sources 442, 444 located at tool shaft distal end 431 of shaft 430 allow the user, for example, to view bodily regions proximate blades 414, 416 in order to navigate blades 414, 416 about a patient's body or while cutting using blades 414, 416.

Figures 7A, 7B:
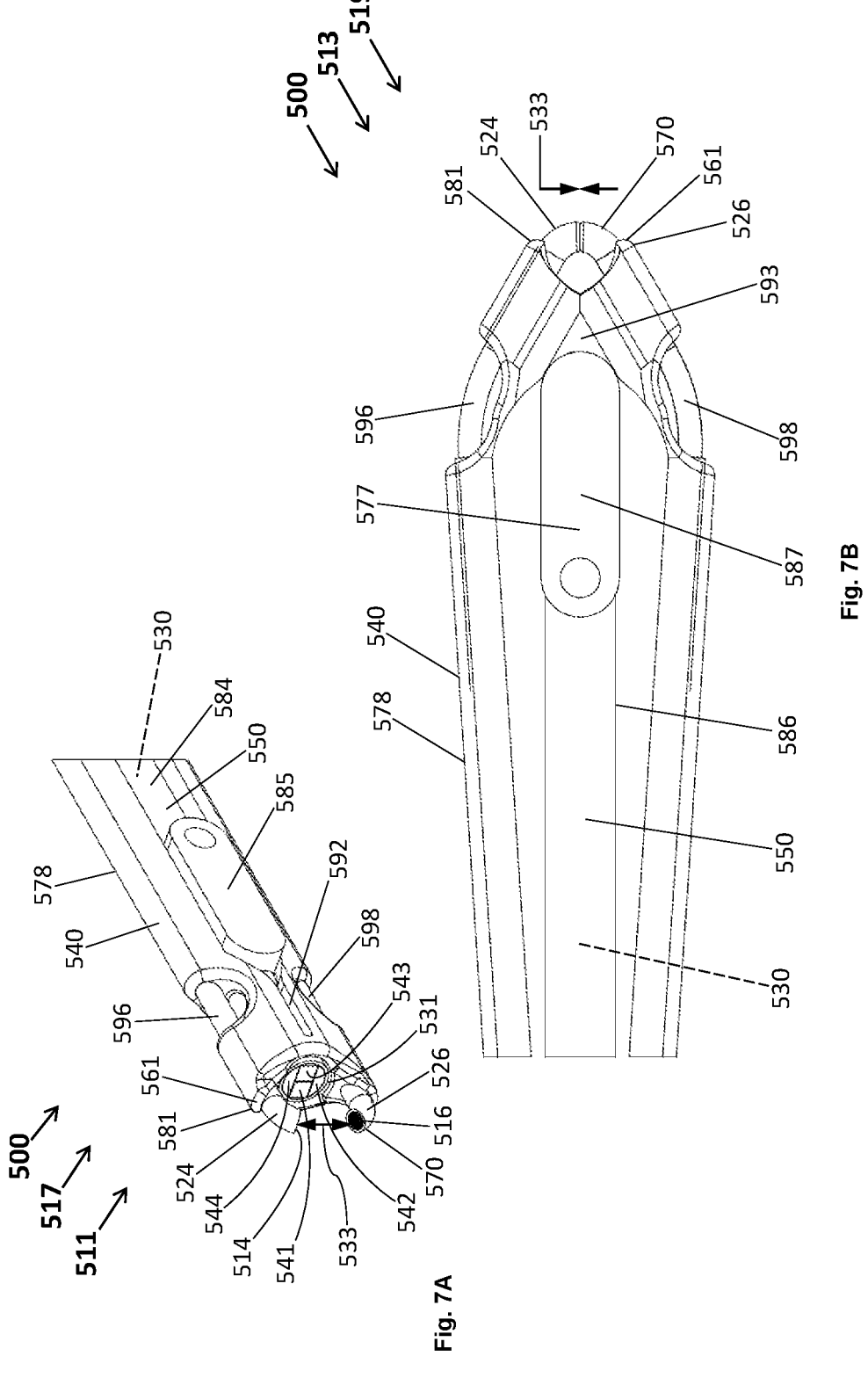
FIG. 7A illustrates by perspective view portions of a fourth exemplary implementation of a microsurgical apparatus at a first operational state.
FIG. 7B illustrates by side view portions the exemplary implementation of the microsurgical apparatus of FIG. 7A at a second operational state.

FIGS. 7A and 7B illustrate portions of tool package 540 of exemplary microsurgical apparatus 500. As illustrated in FIG. 7A, tool package 540 slidably removably receives shaft 530 within sleeve 550 of tool package 540 to engage releaseably tool package 540 with a handle, such as handle 20, 220. As illustrated in FIGS. 7A and 7B, tool package 540 includes tool 570 at tool package distal end 561. In this implementation, tool 570 includes probes 524, 526 with probe elements 514, 516, respectively. Probe element 514 may be, for example, a light source formed as the terminus of a fiberoptic bundle or may include an image sensor. Probe element 516 may be, for example, a light source formed as the terminus of a fiberoptic bundle or may include an image sensor. Probe elements 514, 516 may communicate with proximal portions of microsurgical apparatus 500 via fiberoptic bundles or electrical pathways within lumen formed in tubular members 496, 498 that pass proximally through tool package 540 from probes 514, 516, and, thence, to a computer, such as computer 11, and/or a source, such as source 16, wherein the source communicates femtosecond multi-color illumination to one or both probe elements 514, 516. Images sensors 541, 543 in combination with lights sources 542, 544 located at shaft distal end 531 of shaft 530 allow the user, for example, to view bodily regions proximate probes 524, 526 in order to navigate probes 524, 526 about a patient's body or during diagnostic or therapeutic procedures using probes 524, 526.

Wave length(s) of the light delivered by various combinations of light sources 542, 544 and probe elements 514, 516 may be controlled by computer, such as computer 11, to deliver femtosecond multi-color illumination for spectral analysis in real time using various combinations of images sensors 541, 543 and probe elements 514, 516. Such real time femtosecond multi-color computer driven light combined with image processing including spectral analysis of images from various combinations of image sensors 541, 543 and probe elements 514, 516 may, for example, delineate diseased tissue from healthy tissue or contrast arteries and veins. For example, tissue may be interposed between probes 524, 526 and probe element 514 may be formed as a light source that delivers femtosecond multi-color illumination to tissue and probe element 516 may be formed as an image sensor that receives the femtosecond multi-color illumination after passage through the interposed tissue from probe element 514.

Heads 585, 587 form portions of headpiece 577 which is affixed to sleeve 550, and heads 585, 587 are positioned within sheath slots 584, 586, respectively, when probes 524, 526 are in disengaged position 511 illustrated in FIG. 7A. Probes 524, 526 cooperate with sheath 578 so that length 533 between probes 524, 526 is diminished as heads 585, 587 are inserted into slits 592, 593 from sheath slots 584, 586, respectively, by distal advancement of sleeve 550 to position probes 524, 526 in engaged position 513, as illustrated in FIG. 7B. Length 533 between probes 524, 526 is increased as heads 585, 587 are expelled proximally from slits 592, 593 into sheath slots 584, 586, respectively, by proximal withdrawal of sleeve 550 to position probes 524, 526 from engaged position 513 to disengaged position 511. Sleeve 550 may be advanced distally and withdrawn proximally to position probes 524, 526 between engaged position 513 at second operational state 519 of microsurgical apparatus 500 and disengaged position 511 at first operational state 517 of microsurgical apparatus 500, respectively, generally in the same manner as in microsurgical apparatus 10, 200. Probes 524, 526 may be positioned from disengaged position 511 into engaged position 513, for example, to interpose tissue between probes 524, 526 for examination using probe elements 514, 516.

Figures 8A, 8B:
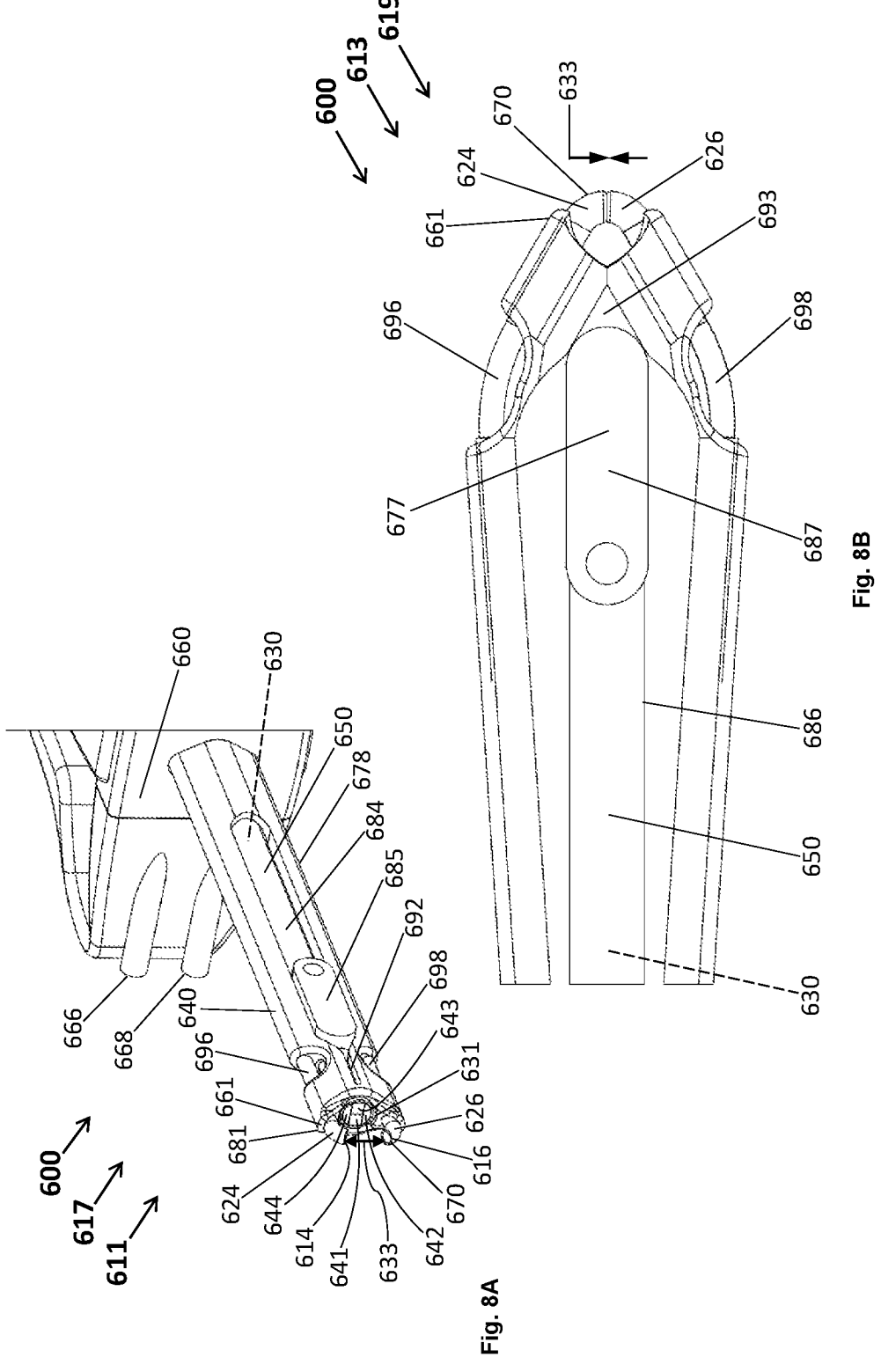
FIG. 8A illustrates by perspective view portions of a fifth exemplary implementation of a microsurgical apparatus at a first operational state.
FIG. 8B illustrates by side view portions the exemplary implementation of the microsurgical apparatus of FIG. 8A at a second operational state; and, FIG. 9 illustrates by process flow chart exemplary method of use of a microsurgical apparatus, such as the exemplary microsurgical apparatus of FIG. 1, 5A, 6A, 7A, 8A.

FIGS. 8A and 8B illustrate portions of tool package 640 of exemplary microsurgical apparatus 600. As illustrated in FIG. 8A, tool package 640 slidably receives shaft 630 within sleeve 650 of tool package 640 to engage releaseably tool package 640 with a handle, such as handle 20, 220. As illustrated in FIGS. 8A and 8B, tool package 640 includes tool 670 at tool package distal end 661. In this implementation, tool 670 includes nozzles 624, 626 with apertures 614, 616, respectively. Fluid may flow into, out of, or into and out of apertures 614, 616 of nozzles 624, 626 in various combinations. For example, fluid may flow out of aperture 614 to irrigate tissue and then be withdrawn by vacuum back into aperture 616. As illustrated in FIG. 8A, tubular members 696, 698 form lumen for fluid communication between ports 666, 668 positioned on actuator 660 and nozzles 624, 626.

Image sensors 641, 643 located at shaft distal end 631 allow the user, for example, to view bodily regions proximate nozzles 624, 626 as illuminated by light sources 642, 644 also located at shaft distal end 631 in order to navigate nozzles 624, 626 about a patient's body or during diagnostic or therapeutic procedures using nozzles 624, 626.

Heads 685, 687 are formed as portions of headpiece 677 which is affixed to sleeve 650, and heads 685, 687 are positioned within sheath slots 684, 686 of sheath 678, respectively, when nozzles 624, 626 are in disengaged position 611 illustrated in FIG. 8A. Nozzles 624, 626 cooperate with sheath 678 and with tubular members 696, 698 so that length 633 between nozzles 624, 626 is diminished as heads 685, 687 are inserted into slits 692, 693 from sheath slots 684, 686, respectively, by distal advancement of sleeve 650 to position nozzles 624, 626 in engaged position 613 illustrated in FIG. 8B. Length 633 between nozzles 624, 626 is increased as heads 685, 687 are withdrawn proximally from slits 692, 693 into sheath slots 684, 686, respectively, by proximal withdrawal of sleeve 650 thereby positioning nozzles 624, 626 from engaged position 613 to disengaged position 611. Sleeve 650 may be advanced distally and withdrawn proximally to position nozzles 624, 626 between engaged position 613 at second operational state 619 of microsurgical apparatus 600 and disengaged position 611 at first operational state 617 of microsurgical apparatus 600, respectively, generally in the same manner as in microsurgical apparatus 10, 200. Nozzles 624, 626 are positioned from disengaged position 611 into engaged position 613, for example, to interpose tissue between nozzles 624, 626 for irrigation using saline, evacuation of fluids such as blood, or simultaneous irrigation and evacuation during diagnostic or therapeutic procedures.

In operation of a microsurgical apparatus, such as microsurgical apparatus 10, 200, 400, 500, 600, a tool package, such as tool package 40, 240, 440, 540, 640, is releaseably replaceably received by a shaft, such as shaft 30, 230, 430, 530, 630. The tool package includes a tool, such as tool 70, 270, 470, 570, 670. The user may then insert the tool including at least portions of the tool package into a body of a patient to diagnose, to deliver therapy, or to both diagnose and deliver therapy to the patient at a site within the body. In certain applications, the tool may be used superficially about the body. One or more light sources, such as light sources 42, 44, 242, 244, 442, 444, 542, 544, 642, 644, located about shaft distal end, such as shaft distal end 31, 231, 431, 531, 631, illuminate bodily regions proximate the tool package distal end, such as tool package distal end 61, 261, 461, 561, 661, for viewing by one or more image sensors, such as image sensors 41, 43, 241, 243, 441, 443, 541, 543, 641, 643, also located at shaft distal end. The light source(s) and image sensor(s) may communicate with a computer including a display, such as computer 11 and display 14. The user may control the light source(s) using the computer including control of light intensity or light wavelength(s) emitted by the light source(s). The user may view distally of the tool using the image sensor(s) illuminated by the light source(s) using the display in order to navigate the tool to a site within the body or while engaging in diagnosis or the delivery of therapy at the site.

When the tool is positioned within the patient, the user may manipulate an actuator, such as actuator 60, 260, 460, 560, 660, by compressing or releasing actuator arms, such as actuator arms 72, 74, 272, 274, in order to alter the microsurgical apparatus between a first operational state, such as first operational state 17, 217, 417, 517, 617, and second operational state, such as second operational state 19, 219, 419, 519, 619, to correspondingly manipulate the tool between a disengaged position, such as disengaged position 111, 311, 411, 511, 611, and an engaged position, such as engaged position 113, 313, 413, 513, 613.

In certain implementations electrical power may be communicated to the tool via electrical pathways, such as electrical pathways 36, 38, 46, 48, and/or via tubular members, such as tubular members 96, 98, 296, 298, 496, 498, 596, 598, 696, 698, so that, for example, the tool may be cauterize tissues at the treatment site. The tubular members may define lumen, for example, containing fiberoptic pathways for the communication of light with the tool or the communication of fluid(s) with the tool or with the tool package distal end. For example, the tubular members may, at least in part, communicate fluidly between nozzles, such as nozzles 436a, 436b, 624, 626 disposed generally about the tool packaged distal end and ports, such as ports 466, 468, 666, 668, disposed generally proximate the handle.

The user may control the communication of electrical power to the tool using an external input device, such as external input device 13. The communication of fluid with the nozzle(s) may be controlled, at least in part, by the computer, and the communication of fluid with the nozzle(s) may be controlled, at least in part, by the external input device, as would be readily recognized by those of ordinary skill in the art upon study of this disclosure. A source, such as source 16, may, for example, communicate light, electrical power, fluid(s), or combinations thereof with the tool, image sensor(s), light source(s), and/or nozzle(s), as may be directed, at least in part, by the computer.

The user may withdraw the entirety of the tool package including the tool from the patient. With the tool package withdrawn from the patient, the user may then release a tool package detent, such as tool package detent 56, 57, 258, of the tool package from engagement with a detent, such as detent 27, 259, of the handle, such as handle 20, 220, and then slidably remove the tool package from the shaft. A different tool package may then be slidably engaged with the shaft, lockably releasably engaged with the handle using the tool package detent and detent, and then applied to the patient. The tool package removed from the shaft may then be discarded following removal. Accordingly, various tool packages that may have tools with various functionalities may be interchangeably received over the shaft and releasably engaged with the handle during the course of diagnosis, treatment, or diagnosis and treatment with the microsurgical apparatus. The various tool packages may then be discarded following use and subsequent removal from the shaft during the course of diagnosis, treatment, or diagnosis and treatment with the microsurgical apparatus.

Figure 9:
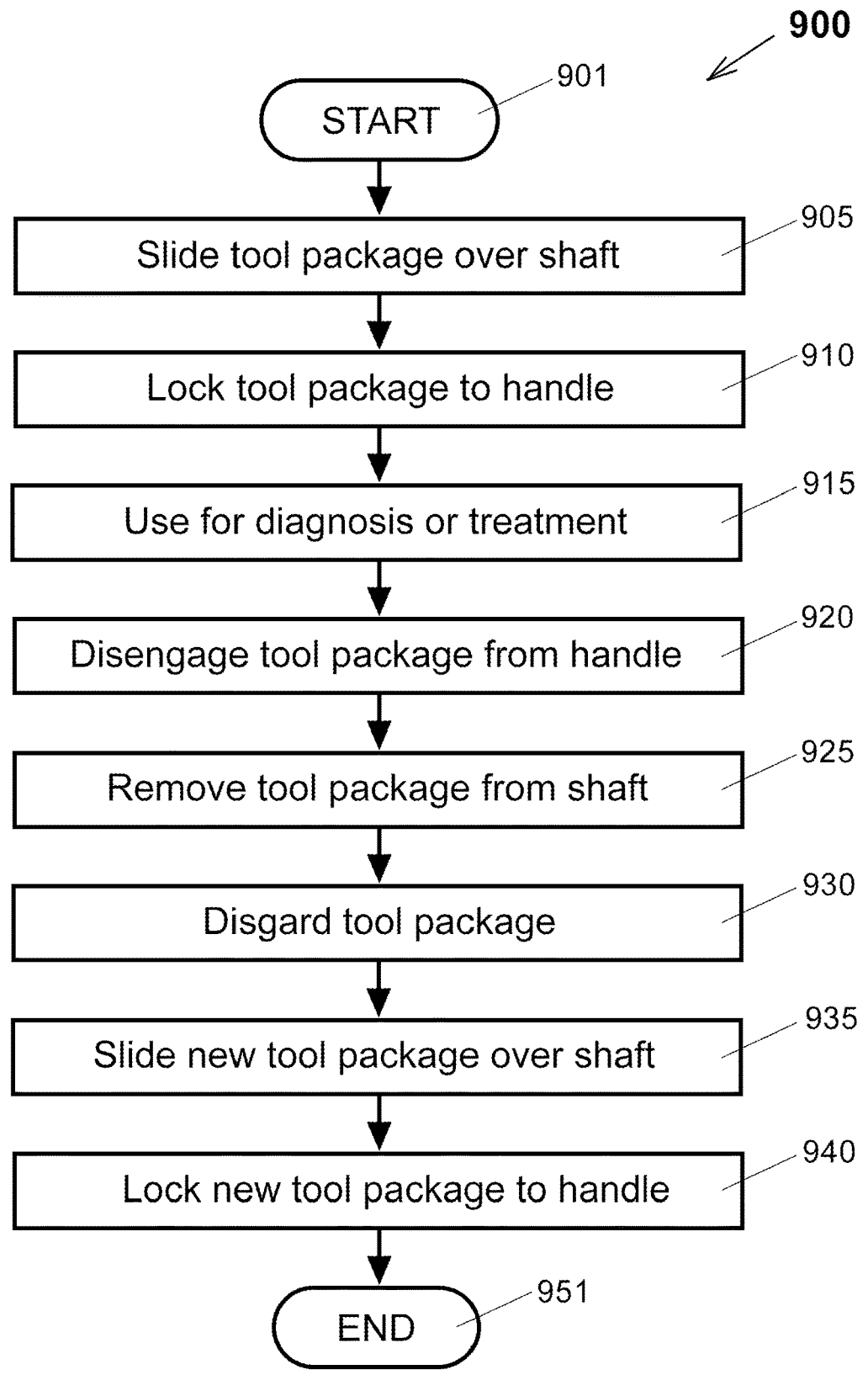

An exemplary method of use of the microsurgical apparatus is illustrated in FIG. 9. As illustrated in FIG. 9, method of use 900 is entered at step 901. At step 905, the tool package is slidably received over the shaft. At step 910, the tool package is lockably engaged with the handle.

A patient is then diagnosed, treated, or diagnosed and treated using the tool, at step 915. Image sensor(s) illuminated by light source(s) may be used to guide the tool into position or to view the tool during diagnosis or therapy. Laser-based femtosecond multi-color illumination may illuminate tissue and spectral analysis of images, such as image 18, from image sensors may be used for diagnosis or to guide the tool.

At step 920, the tool package is disengaged from the handle after use. At step 925, the tool package is removed from the shaft. The tool package is discarded at step 930.

At step 935, a new tool package is slidably received over the shaft, and then lockably releasably engaged with the handle, at step 940. The new tool package may now be used for diagnosis, treatment, or diagnosis and treatment of the patient. Methods 900 terminates at step 951.

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. The Abstract is not intended to identify key elements of the apparatus and methods disclosed herein or to delineate the scope thereof. Upon study of this disclosure and the exemplary implementations herein, one of ordinary skill in the art may readily recognize that various changes, modifications, and variations can be made thereto without departing from the spirit and scope of the inventions as defined in the following claims.

The invention claimed is:

1. A microsurgical apparatus comprising:

a sleeve defining a sleeve lumen extending between a sleeve proximal end of the sleeve and a sleeve distal end of the sleeve, the sleeve lumen being open at the sleeve proximal end to receive a shaft by insertion of the shaft into the sleeve lumen through the sleeve proximal end, the sleeve lumen being open at the sleeve distal end to expose a shaft distal end of the shaft received within the sleeve lumen;

a tool disposed at least in part distal of the sleeve distal end; and a sheath that overlays at least portions of the sleeve, the sheath in mechanical cooperation with the tool and in mechanical cooperation with the sleeve to alter the tool between an engaged position by the collinear distal advancement of the sleeve to deform elastically the sheath and a disengaged position by the collinear proximal withdrawal of the sleeve to relieve elastic deformation of the sheath.

2. The apparatus of claim 1, further comprising:

an actuator disposed in mechanical cooperation with proximal portions of the sleeve to effectuate the col-linear distal advancement and the collinear proximal withdrawal of the sleeve by alteration of the actuator between a first actuator position and a second actuator position.

3. The apparatus of claim 2, further comprising:

a slit formed on a distal portion of the sheath; and a head disposed on the sleeve to be inserted into the slit by the collinear distal advancement of the sleeve to deform elastically the sheath thereby altering the tool into the engaged position.

4. The apparatus of claim 1, further comprising:

an image sensor adapted to communicate with a computer, the image sensor disposed on the shaft distal end of the shaft to view the tool, the shaft being received within the sleeve lumen.

5. The apparatus of claim 1, wherein the shaft is received by the sleeve lumen.

6. The apparatus of claim 1, further comprising:

a first image sensor and a second image sensor disposed on the shaft distal end of the shaft to view distally of the shaft distal end.

7. The apparatus of claim 1, further comprising:

a light source disposed on the shaft distal end of the shaft to emit light from the shaft distal end.

8. The apparatus of claim 7, wherein light being emitted by the light source is adapted to be controlled by a computer.

9. The apparatus of claim 7, wherein the light source is formed as a terminus of a fiberoptic bundle.

10. The apparatus of claim 7, wherein the light source emits laser-based femtosecond multi-color illumination.

11. The apparatus of claim 7, wherein the light source comprises a light emitting diode (LED).

12. The apparatus of claim 7, wherein the light source emits light from a laser.

13. The apparatus of claim 1, further comprising:

an electrical pathway disposed between the sleeve proximal end and the tool to communicate electrically with the tool.

14. The apparatus of claim 1, further comprising:

a fluid pathway disposed between the sleeve proximal end and the tool to communicate fluidly with the tool.

15. The apparatus of claim 1, further comprising:

a fiberoptic pathway disposed between the sleeve proximal end and the sleeve distal end to communicate light therethrough.

16. The apparatus of claim 1, wherein the tool comprises jaws configured to grasp tissue as the tool is altered into the engaged position.

17. The apparatus of claim 1, further comprising:

a handle disposed at a shaft proximal end of the shaft, the handle releaseably securable to the sleeve with the shaft received within the sleeve lumen.

18. The apparatus of claim 1, wherein the tool comprises electrodes for bipolar electrosurgery.

19. The apparatus of claim 1, wherein the tool comprises one or more nozzles to communicate fluid therethrough.

20. The apparatus of claim 1, further comprising:

two or more image sensors disposed on the shaft distal end of the shaft that cooperate with a display to present an image of bodily regions proximate the tool, the image having depth and orientation.

* * * * *